United States Patent
Roeber et al.

(10) Patent No.: US 12,239,573 B2
(45) Date of Patent: Mar. 4, 2025

(54) DRUG THERAPY DELIVERY SYSTEMS AND METHODS

(71) Applicant: W. L. Gore & Associates, Inc., Newark, DE (US)

(72) Inventors: Peter J. Roeber, Oxford, PA (US); Jeffrey C. Towler, Wilmington, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 169 days.

(21) Appl. No.: 17/272,609

(22) PCT Filed: Aug. 29, 2019

(86) PCT No.: PCT/US2019/048759
§ 371 (c)(1),
(2) Date: Mar. 1, 2021

(87) PCT Pub. No.: WO2020/047221
PCT Pub. Date: Mar. 5, 2020

(65) Prior Publication Data
US 2021/0346197 A1 Nov. 11, 2021

Related U.S. Application Data

(60) Provisional application No. 62/724,425, filed on Aug. 29, 2018.

(51) Int. Cl.
*A61F 9/00* (2006.01)
(52) U.S. Cl.
CPC .................. *A61F 9/0017* (2013.01)
(58) Field of Classification Search
CPC .... A61F 9/0017; A61F 9/00781; A61F 9/007; A61F 2202/30028; A61F 2250/0003;
(Continued)

(56) References Cited

U.S. PATENT DOCUMENTS 3,618,604 A 11/1971 Ness
3,683,928 A 8/1972 Kuntz
(Continued)

FOREIGN PATENT DOCUMENTS

AU 06600/12 B2 6/1995
AU 2014280907 A1 1/2015
(Continued)

OTHER PUBLICATIONS

Ando et al., Ten-year experience with handmade trileaflet polytetrafluoroethylene valved conduit used for pulmonary reconstruction. The Journal of Thoracic and Cardiovascular Surgery, Jan. 2009, vol. 137, No. 1, pp. 124-131.
(Continued)

*Primary Examiner* — Ariana Zimbouski
*Assistant Examiner* — Timothy L Flynn
(74) *Attorney, Agent, or Firm* — Nelson Mullins Riley & Scarborough LLP

(57) ABSTRACT

Ocular medicament delivery devices are disclosed. In various embodiments, the ocular medicament delivery devices include multiple microporous layers arranged together to form a microporous body configured to meter dispensing of a medicament to surrounding tissues. In some embodiments, the ocular medicament delivery devices include one or more portions configured to resist tissue ingrowth, and one or more portions configured to permit tissue ingrowth. In some embodiments, the ocular medicament delivery devices deliver one or more medicaments useful in the treatment of glaucoma.

26 Claims, 5 Drawing Sheets

(58) Field of Classification Search
CPC .......... A61M 27/00; A61M 2205/3334; A61M 2210/0612; A61M 2205/3341; A61M 2205/04; A61K 9/7023; A61K 9/7084; A61K 9/7092

See application file for complete search history.

(56) References Cited

U.S. PATENT DOCUMENTS

| | | | |
|---|---|---|---|
| 3,828,777 A | 8/1974 | Ness | |
| 3,960,150 A | 6/1976 | Hussain et al. | |
| 3,962,414 A | 6/1976 | Michaels | |
| 4,014,335 A | 3/1977 | Arnold | |
| 4,182,342 A | 1/1980 | Smith | |
| 4,186,184 A | 1/1980 | Zaffaroni | |
| 4,579,221 A | 4/1986 | Corella | |
| 4,729,761 A | 3/1988 | White | |
| 4,759,759 A | 7/1988 | Walker et al. | |
| 5,037,434 A | 8/1991 | Lane | |
| 5,147,647 A | 9/1992 | Darougar | |
| 5,163,955 A | 11/1992 | Love et al. | |
| 5,282,851 A | 2/1994 | Jacob-LaBarre | |
| 5,378,475 A | 1/1995 | Smith et al. | |
| 5,423,777 A | 6/1995 | Tajiri et al. | |
| 5,476,445 A | 12/1995 | Baerveldt et al. | |
| 5,676,679 A | 10/1997 | Simon et al. | |
| 5,681,275 A | 10/1997 | Ahmed | |
| 5,702,414 A | 12/1997 | Richter et al. | |
| 5,708,044 A | 1/1998 | Branca | |
| 5,713,953 A | 2/1998 | Vallana et al. | |
| 5,773,019 A | 6/1998 | Ashton et al. | |
| 5,861,028 A | 1/1999 | Angell | |
| 5,882,327 A | 3/1999 | Jacob | |
| 5,928,281 A | 7/1999 | Huynh et al. | |
| 5,935,163 A | 8/1999 | Gabbay | |
| 6,050,970 A | 4/2000 | Baerveldt | |
| 6,074,419 A | 6/2000 | Healy et al. | |
| 6,086,612 A | 7/2000 | Jansen | |
| 6,142,969 A | 11/2000 | Nigam | |
| 6,171,335 B1 | 1/2001 | Wheatley et al. | |
| 6,174,331 B1 | 1/2001 | Moe et al. | |
| 6,186,974 B1 | 2/2001 | Allan et al. | |
| 6,197,143 B1 | 3/2001 | Bodnar | |
| 6,254,636 B1 | 7/2001 | Peredo | |
| 6,261,256 B1 | 7/2001 | Ahmed | |
| 6,283,995 B1 | 9/2001 | Moe et al. | |
| 6,287,338 B1 | 9/2001 | Sarnowski et al. | |
| 6,364,905 B1 | 4/2002 | Simpson et al. | |
| 6,432,542 B1 | 8/2002 | Tsai | |
| 6,450,984 B1 | 9/2002 | Lynch et al. | |
| 6,471,689 B1 * | 10/2002 | Joseph ................ | A61M 5/1723 424/424 |
| 6,541,589 B1 | 4/2003 | Baillie | |
| 6,562,069 B2 | 5/2003 | Cai et al. | |
| 6,562,446 B1 | 5/2003 | Totsuka | |
| 6,613,086 B1 | 9/2003 | Moe et al. | |
| 6,613,087 B1 | 9/2003 | Healy et al. | |
| 6,696,526 B1 | 2/2004 | Kaulbach et al. | |
| 6,699,210 B2 | 3/2004 | Williams et al. | |
| 6,699,211 B2 | 3/2004 | Savage | |
| 6,713,081 B2 | 3/2004 | Robinson et al. | |
| 6,881,197 B1 | 4/2005 | Nigam | |
| 6,994,666 B2 | 2/2006 | Shannon et al. | |
| 7,018,404 B2 | 3/2006 | Holmberg et al. | |
| 7,261,732 B2 | 8/2007 | Justino | |
| 7,306,729 B2 | 12/2007 | Bacino et al. | |
| 7,320,705 B2 | 1/2008 | Quintessenza | |
| 7,331,993 B2 | 2/2008 | White | |
| 7,361,189 B2 | 4/2008 | Case et al. | |
| 7,462,675 B2 | 12/2008 | Chang et al. | |
| 7,531,611 B2 | 5/2009 | Sabol et al. | |
| 7,604,663 B1 | 10/2009 | Reimink et al. | |
| 7,833,565 B2 | 11/2010 | O'Connor et al. | |
| 7,862,610 B2 | 1/2011 | Quintessenza | |
| 7,883,717 B2 | 2/2011 | Varner et al. | |
| 8,216,631 B2 | 7/2012 | O'Connor et al. | |
| 8,219,229 B2 | 7/2012 | Cao et al. | |
| 8,246,676 B2 | 8/2012 | Acosta et al. | |
| 8,267,994 B2 | 9/2012 | Jin | |
| 8,273,101 B2 | 9/2012 | Garcia et al. | |
| 8,303,647 B2 | 11/2012 | Case | |
| 8,399,006 B2 | 3/2013 | de Juan, Jr. et al. | |
| 8,545,430 B2 | 10/2013 | Silvestrini | |
| 8,556,960 B2 | 10/2013 | Agnew et al. | |
| 8,623,395 B2 * | 1/2014 | de Juan, Jr. ........... | A61F 9/0017 604/6.12 |
| 8,632,489 B1 | 1/2014 | Ahmed | |
| 8,637,144 B2 | 1/2014 | Ford | |
| 8,690,939 B2 | 4/2014 | Miller | |
| 8,834,406 B2 | 9/2014 | Snyder et al. | |
| 8,834,911 B2 | 9/2014 | Glezer et al. | |
| 8,888,734 B2 | 11/2014 | Nissan et al. | |
| 8,961,593 B2 | 2/2015 | Bonhoeffer et al. | |
| 8,961,599 B2 | 2/2015 | Bruchman et al. | |
| 8,961,600 B2 | 2/2015 | Nissan et al. | |
| 9,139,669 B2 | 9/2015 | Xu et al. | |
| 9,155,610 B2 | 10/2015 | Soletti et al. | |
| 9,155,618 B2 | 10/2015 | Kalmann et al. | |
| 9,216,108 B2 | 12/2015 | Jain et al. | |
| 9,259,313 B2 | 2/2016 | Wheatley | |
| 9,301,835 B2 | 4/2016 | Campbell et al. | |
| 9,301,837 B2 | 4/2016 | Beith | |
| 9,326,891 B2 | 5/2016 | Horvath et al. | |
| 9,364,322 B2 | 6/2016 | Conklin et al. | |
| 9,370,444 B2 | 6/2016 | Cunningham, Jr. | |
| 9,375,347 B2 | 6/2016 | Stergiopulos | |
| 9,539,089 B2 | 1/2017 | Beith | |
| 9,572,713 B2 | 2/2017 | Lind et al. | |
| 9,636,219 B2 | 5/2017 | Keidar et al. | |
| 9,636,254 B2 | 5/2017 | Yu et al. | |
| 9,655,720 B2 | 5/2017 | Bluestein et al. | |
| 9,675,453 B2 | 6/2017 | Guttenberg et al. | |
| 9,833,314 B2 | 12/2017 | Corbett | |
| 9,849,629 B2 | 12/2017 | Zagl et al. | |
| 9,987,120 B2 | 6/2018 | Soletti et al. | |
| 9,999,500 B2 | 6/2018 | Greenslet et al. | |
| 10,052,200 B2 | 8/2018 | Chung et al. | |
| 10,195,023 B2 | 2/2019 | Wrobel | |
| 10,299,915 B2 | 5/2019 | Edelman et al. | |
| 10,307,292 B2 | 6/2019 | Litvin | |
| 10,398,593 B2 | 9/2019 | Erickson et al. | |
| 10,398,707 B2 | 9/2019 | Hughes | |
| 10,413,402 B2 | 9/2019 | Squara | |
| 10,413,403 B2 | 9/2019 | Boden et al. | |
| 10,426,609 B2 | 10/2019 | Edelman et al. | |
| 10,433,955 B2 | 10/2019 | Edelman et al. | |
| 10,512,537 B2 | 12/2019 | Corbett et al. | |
| 10,588,746 B2 | 3/2020 | Bernstein et al. | |
| 10,603,164 B2 | 3/2020 | Girard et al. | |
| 10,849,731 B2 | 12/2020 | Cully et al. | |
| 10,959,941 B2 | 3/2021 | Haffner | |
| 11,351,058 B2 | 6/2022 | Roeber et al. | |
| 11,406,533 B2 | 8/2022 | Roeber et al. | |
| 11,523,940 B2 | 12/2022 | Roeber et al. | |
| 2002/0106395 A1 | 8/2002 | Brubaker | |
| 2002/0110635 A1 | 8/2002 | Brubaker et al. | |
| 2002/0156413 A1 | 10/2002 | Williams et al. | |
| 2002/0165478 A1 | 11/2002 | Gharib et al. | |
| 2002/0198594 A1 | 12/2002 | Schreck | |
| 2003/0014036 A1 | 1/2003 | Varner et al. | |
| 2003/0027332 A1 | 2/2003 | Lafrance et al. | |
| 2003/0088260 A1 | 5/2003 | Smedley et al. | |
| 2003/0094731 A1 | 5/2003 | Simpson | |
| 2003/0109923 A1 | 6/2003 | Chinn et al. | |
| 2003/0229303 A1 | 12/2003 | Haffner et al. | |
| 2004/0024345 A1 | 2/2004 | Gharib et al. | |
| 2004/0215333 A1 | 10/2004 | Duran et al. | |
| 2005/0085892 A1 | 4/2005 | Goto et al. | |
| 2005/0137538 A1 | 6/2005 | Kunzler et al. | |
| 2005/0171507 A1 | 8/2005 | Christian et al. | |
| 2005/0182350 A1 | 8/2005 | Nigam | |
| 2005/0228487 A1 | 10/2005 | Kujawski | |
| 2005/0234546 A1 | 10/2005 | Nugent et al. | |
| 2005/0250788 A1 | 11/2005 | Tu et al. | |
| 2005/0261759 A1 | 11/2005 | Lambrecht et al. | |

(56) References Cited

U.S. PATENT DOCUMENTS

| | | |
|---|---|---|
| 2005/0266047 A1 | 12/2005 | Tu et al. |
| 2005/0267398 A1 | 12/2005 | Protopsaltis et al. |
| 2005/0273033 A1 | 12/2005 | Grahn et al. |
| 2006/0036207 A1 | 2/2006 | Koonmen et al. |
| 2006/0109923 A1 | 5/2006 | Cai et al. |
| 2006/0110429 A1* | 5/2006 | Reiff .................. A61K 9/0051 424/145.1 |
| 2006/0189917 A1 | 8/2006 | Mayr et al. |
| 2006/0195187 A1 | 8/2006 | Stegmann et al. |
| 2006/0258994 A1 | 11/2006 | Avery |
| 2007/0078371 A1 | 4/2007 | Brown et al. |
| 2007/0083184 A1 | 4/2007 | Simpson |
| 2007/0088432 A1 | 4/2007 | Solovay et al. |
| 2007/0118147 A1 | 5/2007 | Smedley et al. |
| 2007/0293872 A1 | 12/2007 | Peyman |
| 2008/0071361 A1 | 3/2008 | Tuval et al. |
| 2008/0082161 A1 | 4/2008 | Woo |
| 2008/0091261 A1 | 4/2008 | Long et al. |
| 2008/0133005 A1 | 6/2008 | Andrieu et al. |
| 2008/0200977 A1 | 8/2008 | Paul et al. |
| 2008/0264993 A1 | 10/2008 | Schulte et al. |
| 2008/0268314 A1 | 10/2008 | Han et al. |
| 2008/0312737 A1 | 12/2008 | Jin |
| 2009/0043321 A1 | 2/2009 | Conston et al. |
| 2009/0157175 A1 | 6/2009 | Benichou |
| 2009/0226731 A1 | 9/2009 | Wittmann et al. |
| 2009/0227933 A1 | 9/2009 | Karageozian |
| 2009/0240215 A1 | 9/2009 | Humayun et al. |
| 2009/0240320 A1 | 9/2009 | Tuval et al. |
| 2009/0299469 A1 | 12/2009 | Kollar |
| 2009/0325030 A1 | 12/2009 | Hamrock et al. |
| 2010/0015200 A1 | 1/2010 | McClain et al. |
| 2010/0082094 A1 | 4/2010 | Quadri et al. |
| 2010/0114006 A1 | 5/2010 | Baerveldt |
| 2010/0114307 A1 | 5/2010 | Agnew et al. |
| 2010/0114309 A1 | 5/2010 | De et al. |
| 2010/0119580 A1 | 5/2010 | Guo et al. |
| 2010/0137981 A1 | 6/2010 | Silvestrini et al. |
| 2010/0161040 A1 | 6/2010 | Braido et al. |
| 2010/0168644 A1 | 7/2010 | Brown |
| 2010/0168839 A1 | 7/2010 | Braido et al. |
| 2010/0185277 A1 | 7/2010 | Braido et al. |
| 2010/0241046 A1 | 9/2010 | Pinchuk et al. |
| 2010/0259748 A1 | 10/2010 | Suzuki |
| 2011/0027579 A1 | 2/2011 | Tate |
| 2011/0028918 A1 | 2/2011 | Hartwell et al. |
| 2011/0098640 A1* | 4/2011 | Horne .................. A61P 27/12 604/93.01 |
| 2011/0112620 A1 | 5/2011 | Du |
| 2011/0118835 A1 | 5/2011 | Silvestrini et al. |
| 2011/0196487 A1 | 8/2011 | Badawi et al. |
| 2011/0244014 A1 | 10/2011 | Williams et al. |
| 2011/0257738 A1 | 10/2011 | Corbett et al. |
| 2011/0270388 A9 | 11/2011 | Stevens |
| 2011/0276128 A1 | 11/2011 | Cao et al. |
| 2011/0282440 A1 | 11/2011 | Cao et al. |
| 2012/0035525 A1 | 2/2012 | Silvestrini |
| 2012/0089073 A1 | 4/2012 | Cunningham, Jr. |
| 2012/0123315 A1 | 5/2012 | Horvath et al. |
| 2012/0123317 A1 | 5/2012 | Horvath et al. |
| 2012/0141914 A1 | 6/2012 | Namba et al. |
| 2012/0165720 A1 | 6/2012 | Horvath et al. |
| 2012/0197175 A1 | 8/2012 | Horvath et al. |
| 2012/0253453 A1 | 10/2012 | Bruchman et al. |
| 2012/0310137 A1 | 12/2012 | Silvestrini |
| 2012/0323315 A1 | 12/2012 | Bruchman et al. |
| 2013/0046379 A1 | 2/2013 | Paolitto et al. |
| 2013/0131577 A1 | 5/2013 | Bronstein et al. |
| 2013/0158381 A1 | 6/2013 | Rickard |
| 2013/0184810 A1 | 7/2013 | Hall et al. |
| 2013/0211314 A1 | 8/2013 | Venkatraman et al. |
| 2013/0218081 A1 | 8/2013 | Roth |
| 2013/0226330 A1 | 8/2013 | Sopori et al. |
| 2013/0274691 A1 | 10/2013 | de Juan, Jr. et al. |
| 2013/0317413 A1 | 11/2013 | Field et al. |
| 2013/0325024 A1 | 12/2013 | Nissan et al. |
| 2013/0325111 A1 | 12/2013 | Campbell et al. |
| 2014/0012371 A1 | 1/2014 | Li |
| 2014/0031927 A1 | 1/2014 | Bruchman et al. |
| 2014/0039468 A1 | 2/2014 | Dunn |
| 2014/0114226 A1 | 4/2014 | Snyder et al. |
| 2014/0128960 A1 | 5/2014 | Greenslet et al. |
| 2014/0154321 A1 | 6/2014 | Ashton |
| 2014/0170204 A1 | 6/2014 | Desai et al. |
| 2014/0186420 A1 | 7/2014 | Utkhede et al. |
| 2014/0214158 A1 | 7/2014 | Board et al. |
| 2014/0236067 A1 | 8/2014 | Horvath et al. |
| 2014/0236068 A1 | 8/2014 | Van et al. |
| 2014/0243729 A1 | 8/2014 | Rynerson |
| 2014/0343475 A1 | 11/2014 | Smedley et al. |
| 2014/0343476 A1 | 11/2014 | Penhasi |
| 2014/0358224 A1 | 12/2014 | Tegels et al. |
| 2015/0005689 A1 | 1/2015 | Horvath et al. |
| 2015/0057595 A1 | 2/2015 | Gunn et al. |
| 2015/0119980 A1 | 4/2015 | Beith et al. |
| 2015/0224200 A1 | 8/2015 | de Juan, Jr. et al. |
| 2015/0224231 A1 | 8/2015 | Bruchman et al. |
| 2015/0320975 A1 | 11/2015 | Simpson et al. |
| 2015/0342875 A1 | 12/2015 | Haffner |
| 2015/0374545 A1 | 12/2015 | Horvath et al. |
| 2016/0015516 A1 | 1/2016 | Bernstein et al. |
| 2016/0038412 A1 | 2/2016 | Guo et al. |
| 2016/0058615 A1 | 3/2016 | Camras et al. |
| 2016/0058616 A1 | 3/2016 | Camras et al. |
| 2016/0067032 A1 | 3/2016 | Soletti et al. |
| 2016/0067093 A1 | 3/2016 | Johnson et al. |
| 2016/0100939 A1 | 4/2016 | Armstrong et al. |
| 2016/0153591 A1 | 6/2016 | Fonfara et al. |
| 2016/0242962 A1 | 8/2016 | Torello et al. |
| 2016/0245432 A1 | 8/2016 | Fonfara et al. |
| 2016/0256321 A1 | 9/2016 | Horvath et al. |
| 2016/0256382 A1 | 9/2016 | Shi et al. |
| 2016/0270958 A1 | 9/2016 | De et al. |
| 2016/0287513 A1 | 10/2016 | Rakic et al. |
| 2016/0296322 A1 | 10/2016 | Edelman et al. |
| 2016/0302965 A1 | 10/2016 | Erickson et al. |
| 2016/0302967 A1 | 10/2016 | Ahn |
| 2016/0331528 A1 | 11/2016 | Parker et al. |
| 2016/0374856 A1 | 12/2016 | Pinchuk et al. |
| 2017/0000610 A1 | 1/2017 | Eppihimer et al. |
| 2017/0014227 A1 | 1/2017 | Boden et al. |
| 2017/0020731 A1 | 1/2017 | Baerveldt |
| 2017/0071729 A1 | 3/2017 | Wrobel |
| 2017/0079779 A1 | 3/2017 | Tabor |
| 2017/0079782 A1 | 3/2017 | Beith |
| 2017/0092974 A1 | 3/2017 | MacPhee |
| 2017/0141423 A1 | 5/2017 | Okada et al. |
| 2017/0156854 A1 | 6/2017 | Hammer |
| 2017/0172794 A1 | 6/2017 | Varner et al. |
| 2017/0189175 A1 | 7/2017 | Justino et al. |
| 2017/0245989 A1 | 8/2017 | Bluestein et al. |
| 2017/0252156 A1 | 9/2017 | Bernstein et al. |
| 2017/0296783 A1 | 10/2017 | Connolly et al. |
| 2017/0367888 A1 | 12/2017 | Brown |
| 2018/0049872 A1 | 2/2018 | Bennett |
| 2018/0071143 A1 | 3/2018 | Silvestrini et al. |
| 2018/0110650 A1 | 4/2018 | Da Silva Curiel et al. |
| 2018/0125632 A1 | 5/2018 | Cully et al. |
| 2018/0126134 A1 | 5/2018 | Cully et al. |
| 2018/0133002 A1 | 5/2018 | Yi et al. |
| 2018/0177592 A1 | 6/2018 | Benichou et al. |
| 2018/0185151 A1 | 7/2018 | Bishop |
| 2018/0263718 A1 | 9/2018 | Griffiths et al. |
| 2018/0263775 A1 | 9/2018 | Shah |
| 2018/0263817 A1 | 9/2018 | Roeber et al. |
| 2018/0263818 A1 | 9/2018 | Roeber et al. |
| 2018/0263819 A1 | 9/2018 | Roeber et al. |
| 2018/0303752 A1 | 10/2018 | Haffner |
| 2018/0344457 A1 | 12/2018 | Gross et al. |
| 2019/0000673 A1 | 1/2019 | Fjield et al. |
| 2019/0015191 A1 | 1/2019 | Berdajs |
| 2019/0046696 A1 | 2/2019 | Parikh et al. |
| 2019/0091014 A1 | 3/2019 | Arcaro et al. |
| 2019/0091015 A1 | 3/2019 | Dienno et al. |

(56) References Cited

U.S. PATENT DOCUMENTS

| | | |
|---|---|---|
| 2019/0105199 A1 | 4/2019 | Ahmed et al. |
| 2019/0125529 A1 | 5/2019 | Colavito et al. |
| 2019/0125530 A1 | 5/2019 | Arcaro et al. |
| 2019/0125531 A1 | 5/2019 | Bennett et al. |
| 2019/0133826 A1 | 5/2019 | Horvath et al. |
| 2019/0167475 A1 | 6/2019 | Horvath et al. |
| 2019/0224047 A1 | 7/2019 | Kao et al. |
| 2019/0282360 A1 | 9/2019 | Colavito et al. |
| 2019/0298572 A1 | 10/2019 | Chu |
| 2019/0343617 A1 | 11/2019 | Sobrino-Serrano et al. |
| 2019/0365531 A1 | 12/2019 | Beith |
| 2020/0113681 A1 | 4/2020 | Armstrong et al. |
| 2020/0121454 A1 | 4/2020 | Spence |
| 2020/0188114 A1 | 6/2020 | Radspinner et al. |
| 2020/0229977 A1 | 7/2020 | Mixter et al. |
| 2020/0337897 A1 | 10/2020 | Sacherman et al. |
| 2021/0315806 A2 | 10/2021 | Haffner |
| 2021/0322217 A1 | 10/2021 | Roeber et al. |
| 2021/0346197 A1 | 11/2021 | Roeber et al. |
| 2022/0080049 A1 | 3/2022 | Garcia et al. |
| 2022/0331162 A1 | 10/2022 | Roeber et al. |
| 2022/0378611 A1 | 12/2022 | Conia et al. |
| 2022/0395397 A1 | 12/2022 | Chu |
| 2023/0054622 A1 | 2/2023 | Roeber et al. |
| 2023/0117758 A1 | 4/2023 | Roeber et al. |
| 2023/0142433 A1 | 5/2023 | Towler et al. |
| 2023/0218286 A1 | 7/2023 | McAlister et al. |

FOREIGN PATENT DOCUMENTS

| | | |
|---|---|---|
| AU | 2015266850 A1 | 12/2016 |
| AU | 2020201236 A1 | 3/2020 |
| AU | 2017439185 A1 | 5/2020 |
| AU | 2021218010 A1 | 9/2021 |
| CA | 2502761 A1 | 4/1997 |
| CA | 2974600 A1 | 10/2015 |
| CA | 2950187 A1 | 12/2015 |
| CN | 1208602 A | 2/1999 |
| CN | 2414757 Y | 1/2001 |
| CN | 1285724 A | 2/2001 |
| CN | 1592640 A | 3/2005 |
| CN | 1976732 A | 6/2007 |
| CN | 101965211 A | 2/2011 |
| CN | 202619978 U | 12/2012 |
| CN | 103179927 A | 6/2013 |
| CN | 103619366 A | 3/2014 |
| CN | 104000684 A | 8/2014 |
| CN | 104114201 A | 10/2014 |
| CN | 105377202 A | 3/2016 |
| CN | 105579001 A | 5/2016 |
| CN | 205198254 U | 5/2016 |
| CN | 107613917 A | 1/2018 |
| EP | 2226624 A1 | 9/2010 |
| EP | 2472297 A1 | 7/2012 |
| EP | 2349147 B1 | 3/2015 |
| EP | 2958530 A1 | 12/2015 |
| EP | 3148491 A1 | 4/2017 |
| EP | 3677229 A1 | 7/2020 |
| EP | 3773377 A1 | 2/2021 |
| GB | 2513194 A | 10/2014 |
| JP | 08-117267 A | 5/1996 |
| JP | 11-505159 A | 5/1999 |
| JP | 2000-513248 A | 10/2000 |
| JP | 2002-521145 A | 7/2002 |
| JP | 2003-301948 A | 10/2003 |
| JP | 2005-500101 A | 1/2005 |
| JP | 2005-121438 A | 5/2005 |
| JP | 2005-294016 A | 10/2005 |
| JP | 2007-521125 | 8/2007 |
| JP | 2008-101926 A | 5/2008 |
| JP | 2010-540079 A | 12/2010 |
| JP | 2011-504127 A | 2/2011 |
| JP | 2011-507631 A | 3/2011 |
| JP | 2012-504031 A | 2/2012 |
| JP | 2012-164647 A | 8/2012 |
| JP | 2013-009982 A | 1/2013 |
| JP | 2014-517720 A | 7/2014 |
| JP | 2014-199348 A | 10/2014 |
| JP | 2014-239034 A | 12/2014 |
| JP | 2015-175815 A | 10/2015 |
| JP | 2016-137278 A | 8/2016 |
| JP | 2017-517363 A | 6/2017 |
| JP | 6655610 B2 | 2/2020 |
| JP | 2020-075162 A | 5/2020 |
| JP | 6872650 B2 | 5/2021 |
| JP | 2021-112598 A | 8/2021 |
| KR | 10-2008-0020259 A | 3/2008 |
| KR | 10-2016-0026107 A | 3/2016 |
| WO | 2001/066037 A2 | 9/2001 |
| WO | 2002/100318 A2 | 12/2002 |
| WO | 2003/007795 A2 | 1/2003 |
| WO | 03/15659 A2 | 2/2003 |
| WO | 2005/076973 A2 | 8/2005 |
| WO | 2007/100408 A2 | 9/2007 |
| WO | 2008/030246 A2 | 3/2008 |
| WO | 2008/030951 A2 | 3/2008 |
| WO | 2008/133852 A1 | 11/2008 |
| WO | 2009/042196 A2 | 4/2009 |
| WO | 2009/137785 A2 | 11/2009 |
| WO | 2010/037141 A1 | 4/2010 |
| WO | 2011/147849 A1 | 12/2011 |
| WO | 2012/018779 A2 | 2/2012 |
| WO | 2012/135603 A2 | 10/2012 |
| WO | 2012/142318 A1 | 10/2012 |
| WO | 2013/090006 A1 | 6/2013 |
| WO | 2013/096854 A3 | 8/2013 |
| WO | 2014/028725 A1 | 2/2014 |
| WO | 2014/130574 A1 | 8/2014 |
| WO | 2014/145811 A1 | 9/2014 |
| WO | 2015/064312 A1 | 5/2015 |
| WO | 2015/065646 A1 | 5/2015 |
| WO | 2015/126332 A1 | 8/2015 |
| WO | 2015/184173 A1 | 12/2015 |
| WO | 2016/033270 A1 | 3/2016 |
| WO | 2016/168686 A1 | 10/2016 |
| WO | 2016/196841 A1 | 12/2016 |
| WO | 2017/156293 A1 | 9/2017 |
| WO | 2018/150392 A1 | 8/2018 |
| WO | 2018/170429 A1 | 9/2018 |
| WO | 2018/170433 A1 | 9/2018 |
| WO | 2018/187714 A1 | 10/2018 |
| WO | 2019/094004 A1 | 5/2019 |
| WO | 2019/154927 A1 | 8/2019 |
| WO | 2020/047221 A1 | 3/2020 |
| WO | 2020/047222 A1 | 3/2020 |

OTHER PUBLICATIONS

Gedde et al., "Treatment Outcomes in the Tube Versus Trabeculectomy (TVT) Study After Five Years of Follow-up", Am J Ophthalmol., vol. 153, No. 5, 2012, pp. 789-803.

Han, et al. "Membrane-tube-type glaucoma shunt device for refractory glaucoma surgery", Glaucoma, Graefes Arch Clin Exp Opthalmol, DOI 10, 1007/s00417-016-3510-z. Springer-Verlag Berlin Heidelberg 2016.

International Preliminary Report on Patentability received for PCT Patent Application No. PCT/US2015/055348, mailed on Apr. 27, 2017, 18 pages.

International Preliminary Report on Patentability received for PCT Patent Application No. PCT/US2018/022922, mailed on Sep. 26, 2019, 9 pages.

International Preliminary Report on Patentability received for PCT Patent Application No. PCT/US2018/022929, mailed on Sep. 26, 2019, 9 pages.

International Preliminary Report on Patentability received for PCT Patent Application No. PCT/US2018/022933, mailed on Sep. 26, 2019, 9 pages.

International Preliminary Report on Patentability received for PCT Patent Application No. PCT/US2019/048759, mailed on Mar. 11, 2021, 12 pages.

International Preliminary Report on Patentability received for PCT Patent Application No. PCT/US2019/048760, mailed on Mar. 11, 2021, 9 pages.

(56) References Cited

OTHER PUBLICATIONS

International Search Report and Written Opinion received for PCT Patent Application No. PCT/US2015/055348, mailed on Apr. 11, 2016, 23 pages.
International Search Report and Written Opinion received for PCT Patent Application No. PCT/US2018/050771, mailed on Feb. 25, 2019, 16 pages.
International Search Report and Written Opinion received for PCT Patent Application No. PCT/US2019/048759, mailed on Feb. 12, 2020, 16 pages.
International Search Report and Written Opinion received for PCT Patent Application No. PCT/US2019/048760, mailed on Dec. 3, 2019, 15 pages.
International Search Report and Written Opinion received for PCT Patent Application No. PCT/US2019/065890, mailed on Mar. 18, 2020, 9 pages.
International Search Report dated Jul. 23, 2018 for PCT/US2018/022922.
International Search Report of PCT/2018/022933 dated Jul. 3, 2018.
International Search Report of PCT/US2018/022929 dated Jun. 28, 2018.
Invitation to Pay Additional Fees received for PCT Patent Application No. PCT/US2019/048759, mailed on Dec. 11, 2019, 10 pages.
Karthikeyan et al., "The concept of ocular inserts as drug delivery systems: An overview", Asian Journal Of Pharmaceutics, vol. 2, No. 4, 2008, pp. 192-200.
Lee et al., "Aqueous-Venous Shunt for Glaucoma A Further Report", Arch Opthalmol, vol. 99, 1981, pp. 2007-2012.
Lee et al., "Aqueous-Venous Shunt in The Rabbit Eye: A Long-Term Follow-Up", Trans. Soc. Ophthal. Sin., vol. 8, 1969, pp. 7-24.
Lee et al., "Aqueous-Venus Shunt for Glaucoma: Report on 15 cases", AnnalOphthal, Oct. 1974, pp. 1083-1088.
Lee et al., "Effect of an Aqueous-Venous Shunt In The Monkey Eye", Canad. J. Ophthal., 3:22, 1968, pp. 22-27.
Lee et al., "Effect of aqueous-venous shunt on rabbit eyes", Inivestigative Ophthalmology, vol. 5, No. 3, 1996, pp. 304-311.
Lee et al., "Glaucoma Microsurgery Aqueous-Venous Shunt Procedure", International Surgery, vol. 57, No. 1, Jan. 1972, pp. 37-41.
Miyazaki, et al., Expanded polytetrafluoroethylene conduits and patches with bulging sinuses and fan-shaped valves in right ventricular outflow tract reconstruction: Multicneter study in Japan. The Journal of Thoracic and Cardiovascular Surgery, Nov. 2011, vol. 142, No. 5, pp. 1122-1129.
Miyazaki, et al., Expanded polytetrafluoroethylene valved conduit and patch with bulging sinuses in right ventricular outflow tract reconstruction. The Journal of Thoracic and Cardiovascular Surgery, Aug. 2007, vol. 134, No. 2, pp. 327-332.
Ootaki et al., Medium-term outcomes after implantation of expanded polytetrafluoroethylene valved conduit. The Annals of Thoracic Surgery, 2018; 105 (3), pp. 843-850.
Rese et al., "Sustained drug delivery in glaucoma", Current Opinion in Ophthalmology, vol. 25, No. 2, 2014, pp. 112-117.
Shinkawa et al., Valved polytetrafluoroethylene conduits for right ventricular outflow tract reconstruction. The Annals of Thoracic Surgery. Jul. 2015; 100(1), pp. 129-137.
Stevenson et al., "Reservoir-Based Drug Delivery Systems Utilizing Microtechnology", Advanced Drug Delivery Reviews, vol. 64, No. 14, 2012, pp. 1590-1602.
Understanding Your Heart Valve. Medtronic USA, Inc., 2006. Pamphlet.
Yamagishi et al. Outflow reconstruction of tetralogy of fallot using a Gore-Tex valve. The Anals of Thoracic Surgery, Dec. 1993; 56(6), pp. 1414-1417.
International Search Report and Written Opinion received for PCT Patent Application No. PCT/US2022/048960, mailed on Mar. 2, 2023, 17 pages.
"Ahmed(Registered) ClearPath Giaucoma Drainage Device Model CP250 and CP350," New World Medical, Inc., Part # 50-0109, pp. 28.
International Search Report and Written Opinion received for PCT Patent Application No. PCT/US2023/010660, mailed on May 24, 2023, 17 pages.
International Search Report and Written Opinion received for PCT Patent Application No. PCT/US2022/031305, mailed on Nov. 7, 2022, 26 pages.
McMenamin et al., "Normal anatomy of the aqueous humour outflow system in the domestic pig eye," Journal of Anatomy, vol. 178, Oct. 1991, pp. 65-77.
Molteno, Anthony C.B., "Molteno3 Glaucoma Drainage Device," Surgical Guide, 0817-SG/GDD, p. 44.
Palioura S. et al., "Role of steroids in the treatment of bacterial keratitis," Clinical Ophthalmology. vol. 10, Jan. 27, 2016, pp. 179-186.
Plemel et al., "Tube shunt surgery in pig eyes: a wet lab teaching model," Canadian Journal of Ophthalmology, vol. 54, Issue 5, Oct. 2019, pp. 585-589.
Shastri, V et. al. Non-Degradable Biocompatible Polymers in Medicine: Past, Present, and Future. Current Pharmaceutical Biotechnology, vol. 4, No. 5, 2003, pp. 331-337 [online], [retrieved on Nov. 8, 2023], Retrieved from the Internet <URL: https://pubmed.ncbi.nlm.nih.gov/14529423/> (Year: 2003).
Wadhawan, A et. al. Gore-tex® versus resolut adapt® GTR membranes with perioglas® in periodontal regeneration. Contemp. Clin. Dent., vol. 3, No. 4, Oct.-Dec. 2012, pp. 406-411 [online], [retrieved on Nov. 8, 2023], Retrieved from the Internet <URL: https://www.ncbi.nlm.nih.gov/pmc/articles/PMC3636825/> (Year: 2012).
"Ahmed(Registered) ClearPath Giaucoma Drainage Device Model CP250 and CP350," New World Medical, Inc., Part # 50-0109, pp. 28. Downloaded Mar. 6, 2020.
"The Ahmed Giaucoma Valve Model FP7," New World Medical, Inc., Part #50-0088 Rev C, URL: htps://www.newworldmedical.com/wp-content/uploads/2020/07/AGV-FP7-IFU-50-0088-Rev-C.pdf, Nov. 2019, pp. 1-28.
Kahook et al., "Location of glaucoma drainage devices relative to the optic nerve," British Journal of Ophthalmol, vol. 90, No. 8, Aug. 2006, pp. 1010-1013.
Lee et al., "Pig eye trabeculectomy-a wet-lab teaching model," Eye, vol. 20, Jan. 28, 2005, pp. 32-37.
Mohammadi et al., "Sheep practice eye for ophthalmic surgery training in skills laboratory," Journal of Cataract and Refractive Surgery, vol. 37, No. 6, Jun. 2011, pp. 987-991.
International Preliminary Report on Patentability received for PCT Patent Application No. PCT/US2023/010660, mailed on Jul. 25, 2024, 10 pages.

\* cited by examiner

DRUG THERAPY DELIVERY SYSTEMS AND METHODS

CROSS-REFERENCE TO RELATED APPLICATION

This application is a national phase application of PCT Application No. PCT/US2019/048759, internationally filed on Aug. 29, 2019, which claims the benefit of Provisional Application No. 62/724,425, filed Aug. 29, 2018, which are incorporated herein by reference in their entireties for all purposes.

BACKGROUND

Aqueous humor is a fluid that fills the anterior chamber of the eye and contributes to the intraocular pressure or fluid pressure inside the eye. Ocular hypertension is a condition in the eye where the intraocular pressure or fluid pressure inside the eye is elevated. Untreated ocular hypertension can lead to disease, including glaucoma, which can result in a gradual and sometimes permanent loss of vision in the afflicted eye.

Many attempts have been made to treat ocular hypertension, and glaucoma in particular. Such attempts include surgical procedures that involve implantation of drainage devices designed to lower the intraocular pressure of the afflicted eye, as well as medicament administration. The goal of these treatments is to improve quality of life and to preserve visual function through a reduction of the intraocular pressure.

Though medicament administration is typically in the form of eyedrops that must be self-administered by the patient, implantable extended drug delivery devices can be employed in certain instances. Implantable extended drug delivery devices typically reside either on the exterior of the eye (e.g., extraocular approaches), or are alternatively implanted within the anterior chamber of the eye (intracameral approaches).

Extraocular approaches to medicament delivery present a variety of challenges. To be effective, the extraocular approach requires transporting, via the biological processes of the eye, a sufficient amount of the medicament through the conjunctival layer of the eye and into the anterior chamber of the eye. Obvious natural mechanisms such as the continual flushing mechanism of the human tear film, as well as the natural barrier to the interior of the eye formed by the conjunctiva, complicate the effectiveness of extraocular approaches, resulting in sub-optimal dose delivery over time. Extraocular approaches therefore sometimes include administration of an excessive amount of the medicament to extend a period of efficacy.

Intracameral approaches, on the other hand, are more invasive approaches requiring a puncture through the various tissue layers of the eye to gain access to, and placement of, the device within the anterior chamber of the eye. Intracameral approaches are additionally complicated where the medicament is administered in association with a device that is absorbable (bioabsorbable), as the degrading nature of the device may lead to the device dislodging and floating within the anterior chamber. Moreover, device removal and replacement again requires trauma to the tissues of the eye.

SUMMARY

According to one example ("Example 1"), an implantable delivery device for dispensing a medicament includes a first microporous layer including a plurality of pores sized to permit tissue ingrowth, a second microporous layer including a plurality of pores sized to permit tissue ingrowth, a third microporous layer coupled to the first microporous layer including a plurality of pores sized to resist tissue ingrowth, and a reservoir for receiving the medicament, the reservoir being defined between the third microporous layer and the second microporous layer, wherein the third microporous layer is configured to meter a rate at which the medicament is eluted from the reservoir when the delivery device is implanted.

According to another example ("Example 2"), further to Example 1, the implantable delivery device further includes a fourth microporous layer coupled to the second microporous layer such that the reservoir is defined between the third microporous layer and the fourth microporous layer.

According to another example ("Example 3"), further to Example 2, the fourth microporous layer includes a plurality of pores sized to resist tissue ingrowth, and wherein the fourth microporous layer is permeable to the medicament.

According to another example ("Example 4"), further to Example 2, the fourth microporous layer is impermeable to the medicament.

According to another example ("Example 5"), further to Example 4, wherein the fourth layer includes an elastomer.

According to another example ("Example 6"), further to any of the preceding Examples, the first microporous layer includes an aperture configured to expose the third microporous layer.

According to another example ("Example 7"), further to any of the preceding Examples, the implantable delivery system includes one or more structural spacers disposed within the reservoir to maintain a separation between the second and third microporous layers.

According to another example ("Example 8"), further to any of the preceding Examples, the reservoir is configured to be refilled and emptied situ.

According to another example ("Example 9"), further to any of the preceding Examples, the reservoir is configured to inflate to accommodate medicament therein.

According to another example ("Example 10"), further to any of the preceding Examples, at least one of the first and second microporous layers include an expanded polytetrafluoroethylene (ePTFE) membrane.

According to another example ("Example 11"), further to any of the preceding Examples, a first portion of the third microporous layer is impermeable to the medicament, and wherein a second portion of the third microporous layer is permeable to the medicament.

According to another example ("Example 12"), further to any of the preceding Examples, the first portion of the third microporous layer includes an elastomer.

According to another example ("Example 13"), further to any of the preceding Examples, the delivery device is implantable within an eye.

According to another example ("Example 14"), further to Example 13, the medicament is an ocular medicament for treating glaucoma.

According to another example ("Example 15"), an implantable delivery device for dispensing a medicament includes a first microporous layer coupled to a second microporous layer to define a reservoir including a first interior surface and an opposing second interior surface, and a body having an exterior surface, wherein the first interior surface is separable from the second interior surface when the reservoir is filled with a medicament, wherein the first interior surface is configured to meter a dispensing of the medicament over a predetermined period of time, and wherein the first interior surface is configured to resist tissue ingrowth, and wherein the exterior surface of the body is configured to permit tissue ingrowth.

According to another example ("Example 16"), further to Example 15, at least a portion the first interior surface is permeable to the medicament.

According to another example ("Example 17"), further to Examples 15 to 16, the second interior surface is impermeable to the medicament.

According to another example ("Example 18"), further to Example 17, the second interior surface includes an elastomer.

According to another example ("Example 19"), further to Examples 15 to 18, the reservoir is configured to be refilled and emptied in situ.

According to another example ("Example 20"), further to Examples 15 to 19, the reservoir is configured to inflate to accommodate medicament therein.

According to another example ("Example 21"), further to Examples 15 to 20, at least one of the first and second microporous layers include an expanded polytetrafluoroethylene (ePTFE) membrane.

According to another example ("Example 22"), further to Examples 15 to 21, a first portion of the first interior surface is impermeable to the medicament, and wherein a second portion of the first interior surface is permeable to the medicament.

According to another example ("Example 23"), further to Example 22, the first portion of the first interior layer includes an elastomer.

According to another example ("Example 24"), further to Examples 15 to 23, the delivery device is implantable within an eye.

According to another example ("Example 25"), further to Examples 15 to 24, the medicament is an ocular medicament for treating glaucoma.

According to another example ("Example 26"), a delivery device for dispensing a medicament includes a microporous body including a first microporous layer, a second microporous layer, and a third microporous layer, the first microporous layer being situated between the second and third microporous layers, the first microporous layer including a plurality of pores sized to resist tissue ingrowth, where the second and third microporous layers each include a plurality of pores sized to permit tissue ingrowth; and a medicament reservoir located between the first microporous layer and the third microporous layer.

According to another example ("Example 27"), further to Example 26, the first microporous layer includes a metering portion for dispensing a medicament over a period of time.

According to another example ("Example 28"), further to Examples 26 to 27, the second and third microporous layers define an exterior of the delivery device.

According to another example ("Example 29"), further to Examples 26 to 28, the first microporous layer is coupled to the second microporous layer.

According to another example ("Example 30"), further to Example 29, the second microporous layer includes an aperture configured to expose the first microporous layer.

According to another example ("Example 31"), further to Examples 26 to 30, the medicament reservoir is configured to be refilled and emptied in situ.

According to another example ("Example 32"), further to Examples 26 to 31, the medicament reservoir is configured to inflate to accommodate medicament therein.

According to another example ("Example 33"), further to Examples 26 to 32, at least one of the first, second, and third microporous layers include an expanded polytetrafluoroethylene (ePTFE) membrane.

According to another example ("Example 34"), further to Examples 26 to 33, wherein the first microporous layer includes a first portion that is permeable to the medicament and a second portion that is impermeable to the medicament, the second portion of the first microporous layer including an elastomer.

According to another example ("Example 35"), further to Examples 26 to 34, wherein the delivery device is implantable within an eye.

According to another example ("Example 36"), further to Examples 27 to 35, the medicament is an ocular medicament for treating glaucoma.

According to another example ("Example 37"), a medicament metering device having an exterior surrounding an interior that defines a medicament reservoir, the device includes a first stratum including a first microporous layer and a second microporous layer, the first microporous layer being configured to resist tissue ingrowth and the second microporous layer being configured to permit tissue ingrowth, the first microporous layer defining a portion of the interior and the second microporous layer defining a portion of the exterior; and a second stratum coupled to the first stratum such that the medicament reservoir is defined between the first and second strata, a portion of the first microporous layer of the first stratum being permeable to a medicament disposable within the medicament reservoir.

According to another example ("Example 38"), further to Example 37, the medicament reservoir is defined between portions of the first and second strata that are not coupled to one another such that the uncoupled portions of the first and second strata are free to deflect relative to one another.

According to another example ("Example 39"), further to Examples 37 to 38, the second stratum includes a third microporous layer and a fourth microporous layer, the third microporous layer of the second stratum being configured to resist tissue ingrowth and the fourth microporous layer of the second stratum being configured to permit tissue ingrowth, wherein the third microporous layer of the second stratum defines a portion of the interior and the fourth microporous layer defines a portion of the exterior.

According to another example ("Example 40"), further to Examples 37 to 39, the first and second microporous layers of the first stratum include expanded polytetrafluoroethylene (ePTFE).

According to another example ("Example 41"), further to Examples 37 to 40, the first microporous layer of the first stratum includes a plurality of pores that sized to resist tissue ingrowth, and wherein the second microporous layer of the first stratum includes a plurality of pores sized to permit tissue ingrowth.

According to another example ("Example 42"), further to Examples 39 to 41, the third microporous layer of the second stratum includes a plurality of pores that sized to resist tissue ingrowth, and wherein the fourth microporous layer of the second stratum includes a plurality of pores sized to permit tissue ingrowth.

According to another example ("Example 43"), further to Examples 39 to 42, the third microporous layer of the second stratum includes an elastomer such that the third microporous layer of the second stratum is impermeable to the medicament.

According to another example ("Example 44"), further to Examples 37 to 43, the first microporous layer of the first stratum includes a first portion that is permeable to the medicament and a second portion that is impermeable to the medicament, the second portion of the first microporous layer of the first stratum including an elastomer.

According to another example ("Example 45"), further to Examples 37 to 44, the delivery device is implantable within an eye.

According to another example ("Example 46"), further to Example 45, the medicament is an ocular medicament for treating glaucoma.

According to another example ("Example 47"), further to any of the preceding Examples, the medicament is included within a fluid suspension of particles.

According to another example ("Example 48"), further to Example 47, wherein the first microporous layer of the first stratum includes a plurality of pores sized to prevent passage of the particles through the first microporous layer.

BRIEF DESCRIPTION OF THE DRAWINGS

The accompanying drawings are included to provide a further understanding of the embodiments of the disclosure and are incorporated in and constitute a part of this specification, illustrate examples, and together with the description serve to explain the principles of the disclosure.

DETAILED DESCRIPTION

Persons skilled in the art will readily appreciate that the various embodiments of the inventive concepts provided in the present disclosure can be realized by any number of methods and apparatuses configured to perform the intended functions. It should also be noted that the accompanying figures referred to herein are not necessarily drawn to scale, but may be exaggerated to illustrate various aspects of the present disclosure, and in that regard, the figures should not be construed as limiting.

The present disclosure relates to systems, devices, and methods for delivering a medicament to an eye of a patient. In various embodiments, the medicament is an ocular medicament that is configured to treat, for example, ocular hypertension and/or glaucoma, by causing the intraocular pressure to decrease from undesirably high levels that may lead to a gradual and sometimes permanent loss of vision in the afflicted eye. In various embodiments, medicament delivery systems according to the instant disclosure are configured to meter drug release rates for one or more different medicaments, and thus may be configured to provide multiple different release rates, including multiple different release rates for multiple medicaments. Some examples of suitable ocular medicaments include therapeutic agents, such as prostaglandin analogs (PGAs) (e.g., latanoprost), or therapeutic agents from other drug classes, including beta-blockers such as timolol, alpha-2-agonists such as brimonidine tartrate, or carbonic anhydrase inhibitors such as dorzolamide, compounds of carbonic anhydrase inhibitors and beta-blockers, and compounds of alpha-agonists and beta-blockers which may be administered in combination with PGAs.

In some embodiments, such medicament delivery systems are configured to be implanted and minimally invasively refillable one or more times in situ without requiring removal of the medicament delivery system from an implantation site. Given the size and subconjunctival target implantation locations, implantation procedures can be performed outside of the operating room, where needle puncture and small incisions are commonly performed. Additionally, some system examples include features for helping reduce micro-movement between the medicament delivery systems and the tissue into which they are implanted. Micro-movement sometimes leads to irritation of the surrounding tissue, which is known to lead to a foreign body tissue response that can cause excessive scar formation, eventual erosion of implanted devices, and/or site infection.

Figure 1A:
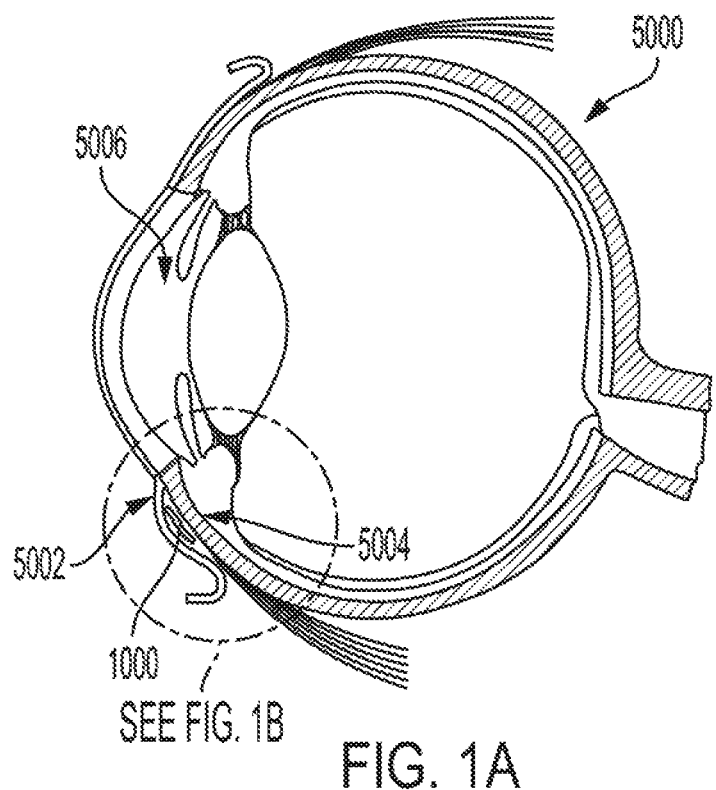
FIG. 1A is an illustration of a medicament delivery system implanted within an eye according to some embodiments.

A medicament delivery system 1000 according to some embodiments is illustrated in FIG. 1A. As illustrated, the medicament delivery system 1000 is implanted within the eye 5000 between the conjunctiva 5002 and the sclera 5004 of the eye 5000. Also shown is an anterior chamber 5006. The medicament delivery system 1000 generally includes one or more portions that are configured to meter drug release from the medicament delivery system 1000, as well as one or more portions that are configured to promote or permit cellular infiltration and/or tissue attachment. The medicament may include a single therapeutic agent (e.g., a medication), or may include multiple therapeutic agents. The medicament delivery system 1000 may be configured to meter drug release rates for multiple different medicaments at multiple different release rates.

Figure 1B:
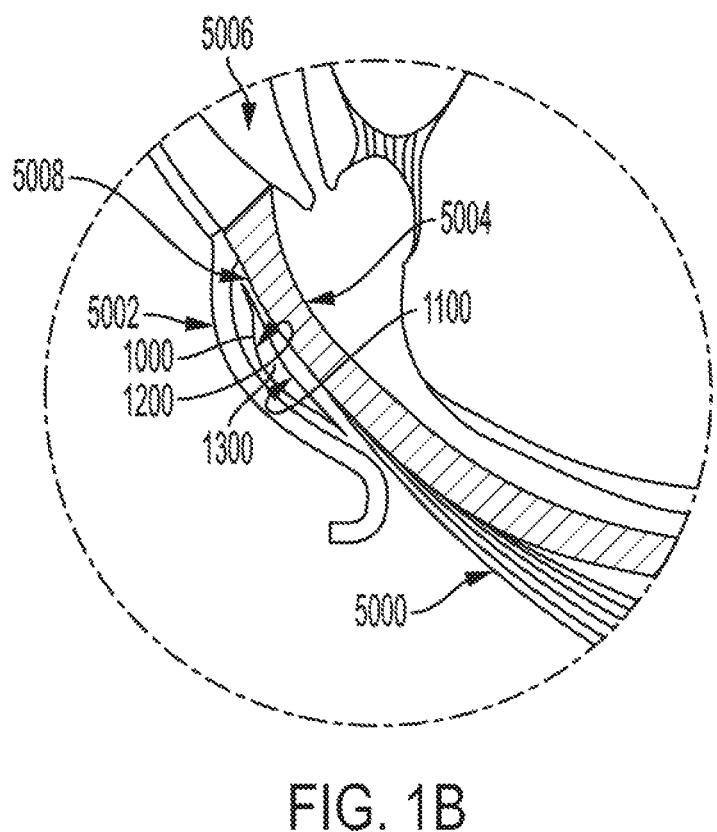
FIG. 1B is a detailed view of FIG. 1A illustrating the medicament delivery system implanted within the eye according to some embodiments.

FIG. 1B is a detail view of region 1B in FIG. 1A, and illustrates the medicament delivery system 1000 implanted within a subconjunctival space 5008. As shown, the subconjunctival space 5008 is a pocket formed between the conjunctiva 5002 and the sclera 5004 of the eye 5000. The subconjunctival space 5008 shown in FIGS. 1A and 1B may be formed according to known methods. In some embodiments, the medicament delivery system 1000 is implantable ab-externally (e.g., from outside of the eye), such as through a conjunctival incision. In some embodiments, a conjunctival radial incision is performed near the limbal junction, and blunt dissection of the conjunctiva is performed to expose the sclera and to form a subconjunctival pocket for placement of the medicament delivery system 1000. In other embodiments, the medicament delivery system 1000 is implanted ab-internally (e.g., from inside the eye), such as through a clear-corneal incision, and placed through the sclera 5004 and into a dissected subconjunctival space 5008.

In some embodiments, the medicament delivery system 1000 may be further secured to the sclera 5004 or other surrounding tissue, such as by way of suturing, adhesives, or according to other known methods. Though the medicament delivery system 1000 may be permanently or semi-permanently secured at the time of implantation, the medicament delivery system 1000 may also initially be temporarily secured (or initially not secured at all), and subsequently secured to the sclera 5004 or other surrounding tissue by one or more portions of medicament delivery system 1000 configured to promote or permit cellular infiltration and tissue attachment.

With continued reference to FIGS. 1A and 1B, the medicament delivery system 1000 includes at least a first stratum 1100 and a second stratum 1200. The first and second strata 1100 and 1200 are generally coupled together in a manner that provides for a medicament reservoir 1300 being defined between the first and second strata 1100 and 1200, as depicted in FIG. 1B. The medicament reservoir 1300 is generally an enclosed spaced within which a medicament can be deposited for subsequent delivery by the medicament delivery system 1000. Generally, the medicament delivery system 1000 is configured to meter a release rate of the medicament disposed within the medicament reservoir 1300 over a designated period of time. For instance, a medicament can be disposed or deposited within the medicament reservoir 1300 and the medicament delivery system 1000 can be configured to release the medicament in accordance with a predetermined therapy regime to treat one or more deficiencies or conditions of the eye.

Moreover, the medicament delivery system 1000 may be minimally invasively refillable and/or emptiable in situ (e.g., without first requiring removal of the medicament delivery system 1000 from the implantation site). In some such embodiments, one or more of the first and second strata 1100 and 1200 are configured such that they may be repeatedly pierced with a cannula during medicament reservoir refilling or emptying operations without significantly jeopardizing the integrity of the first and/or second strata 1100 and 1200. In some embodiments, this integrity may be achieved by coating or imbibing the first and/or second strata 1100 and 1200 with an elastomeric material.

Figure 2:
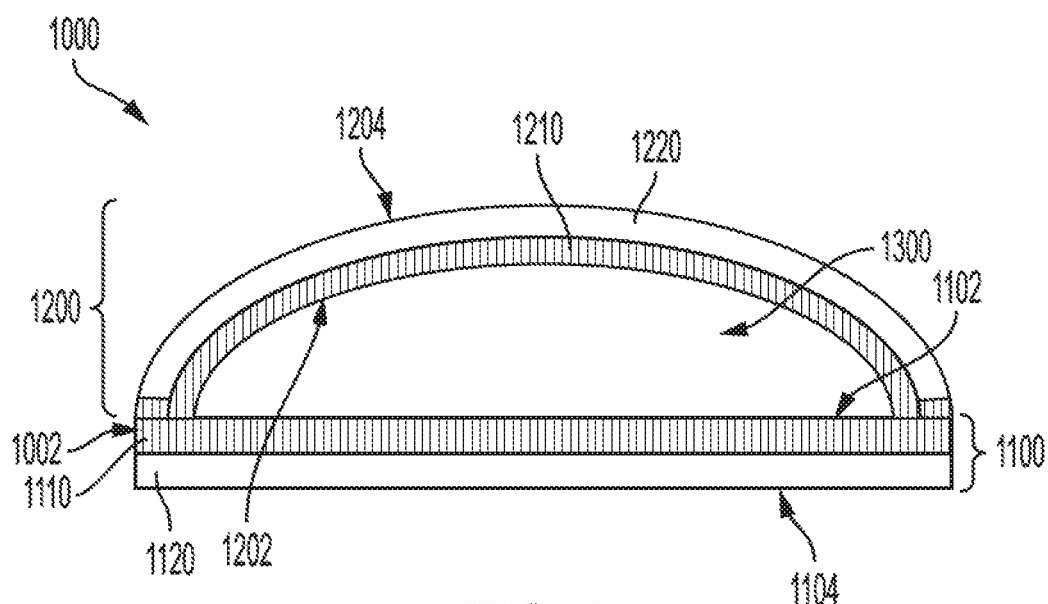
FIG. 2 is a cross-sectional view of the medicament delivery system illustrated in FIG. 4 taken along line 2-2 and in an inflated state according to some embodiments.
Figure 3:
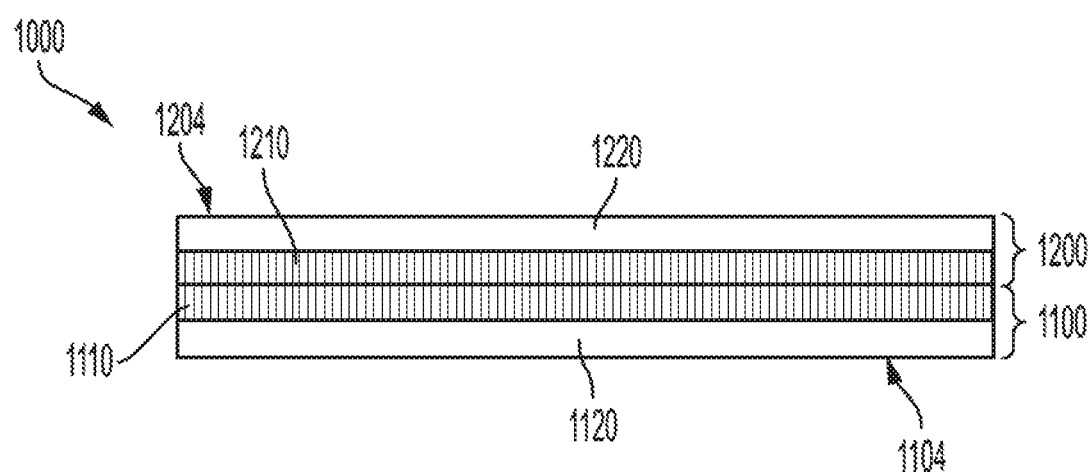
FIG. 3 is a cross-sectional view of the medicament delivery system illustrated in FIG. 4 taken along line 2-2 and in a deflated state according to some embodiments.
Figure 4:
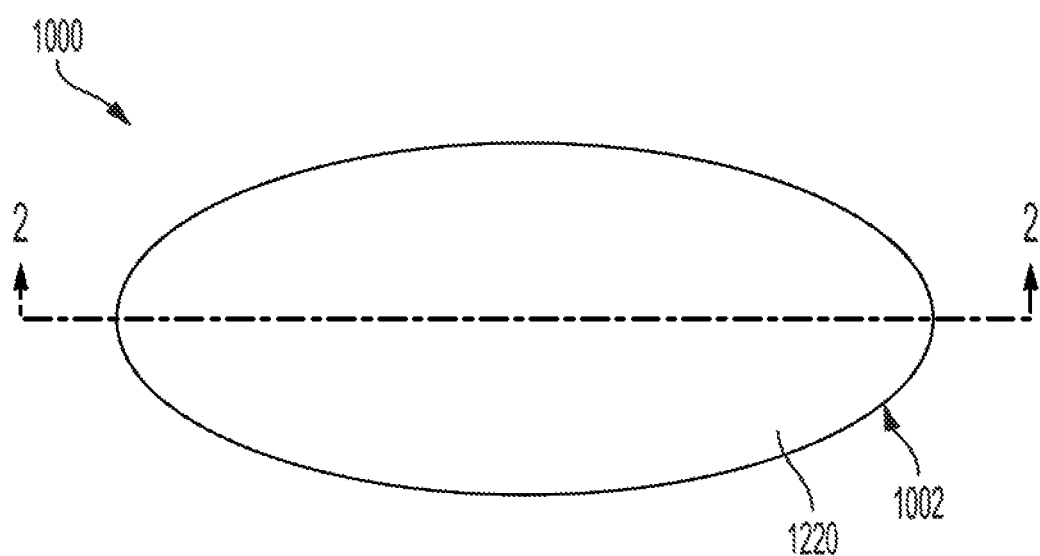
FIG. 4 is a front view of a medicament delivery system according to some embodiments.

With reference now to FIGS. 2-4, a medicament delivery system 1000 is shown. FIG. 2 is a cross-sectional view of the medicament delivery system 1000 shown in an inflated state (i.e., where the medicament reservoir 1300 is inflated such that a separation is defined between the first and second strata 1100 and 1200), taken along line 2-2 of the medicament delivery system illustrated in FIG. 4. In some embodiments, the inflated state corresponds to the presence of a medicament in the medicament reservoir 1300. FIG. 3 is a cross-sectional view of the medicament delivery system 1000 taken along line 2-2 of the medicament delivery system illustrated in FIG. 4, shown in a deflated state, such as when the medicament reservoir 1300 is empty or devoid of a sufficient amount of medicament to cause a separation between the first and second strata 1100 and 1200. FIG. 4 is a front view of a medicament delivery system 1000.

As depicted in FIG. 2, the first and second strata 1100 and 1200 are coupled together along one or more portions of the first and second strata 1100 and 1200, while one or more other portions of the first and second strata 1100 and 1200 remain uncoupled. The uncoupled portions of the first and second strata 1100 and 1200 remain free to separate from one another. In various embodiments, the uncoupled portions of the first and second strata 1100 and 1200 are operable to separate from one another to define the medicament reservoir 1300.

In some embodiments, the first and second strata 1100 and 1200 may be coupled together about a peripheral edge 1002 of the medicament delivery system 1000, as shown in FIG. 2. However, it is to be appreciated that the first and second strata 1100 and 1200 may additionally or alternatively be coupled in other regions, including one or more regions interior to the peripheral edge 1002. The peripheral edge 1002 is generally an edge that extends about the periphery of the medicament delivery system 1000. The peripheral edge 1002 may be uniform, non-uniform, continuous, or discontinuous. For instance, in some embodiments, the peripheral edge 1002 may include one or more radially extending tabs or petals (e.g., the medicament delivery system 1000 may include a scalloped peripheral edge). In some embodiments, these tabs or petals may operate as a coupling region for coupling the medicament delivery system 1000 to surrounding tissue, such as the sclera 5004.

As shown in FIG. 2, the first and second strata 1100 and 1200 are coupled together at the peripheral edge 1002 and/or along a region just radially inwardly of the peripheral edge 1002 to form a coupling region that extends adjacent to the peripheral edge 1002. The coupling region may be annularly shaped and may extend as radially inwardly from the peripheral edge 1002 as desired. As shown in FIG. 2, the medicament reservoir 1300 is defined between the first and second strata 1100 and 1200 where the first and second strata 1100 and 1200 remain uncoupled. It will be appreciated that the first and second strata 1100 and 1200 may additionally be coupled together at a plurality of discrete locations or regions, including one or more locations or regions radially inwardly of the peripheral edge 1002 of the medicament delivery system 1000. Coupling together one or more additional regions interior to the peripheral edge may help to control an inflation profile of the medicament delivery system 1000.

One or more of the first and second strata 1100 and 1200 may be configured to elastically or plastically deform as the medicament reservoir 1300 is inflated. Moreover, in some embodiments, one the first and second strata 1100 and 1200 may be inelastic, which may help to control an expansion profile of the medicament delivery system 1000.

In various embodiments, one or both of the first and second strata 1100 and 1200 includes one or more regions configured to meter a release of medicament. These metering regions may be in the form of membranes, layers, or films, or coatings. In some embodiments, one or more of the first and second strata 1100 and 1200 includes one or more regions configured to permit or promote cellular infiltration or tissue ingrowth and attachment. Cellular infiltration and tissue attachment generally occurs where materials are of a sufficiently porous nature to permit fibroblastic infiltration. Accordingly, the medicament delivery system 1000 may include membranes, layers, films, and/or coatings that are configured to permit tissue ingrowth and attachment.

In at least one embodiment, the first and/or second strata 1100 and 1200 may be formed of a plurality of membrane layers. For example, as shown in FIGS. 2 and 3, the first stratum 1100 may include a first membrane layer 1110 and a second membrane layer 1120. The first and second membrane layers 1110 and 1120 of the first stratum 1100 collectively define the first stratum 1100. It will be appreciated that the first stratum 1100 may include membrane layers in addition to the first and second membrane layers 1110 and 1120.

In some embodiments, one or more of the first and second membrane layers 1110 and 1120 may include a microporous microstructure. For example, one or more of the first and second membrane layers 1110 and 1120 may include biocompatible materials such as expanded polytetrafluoroethylene (ePTFE). Additionally, one or more of first and second membrane layers 1110 and 1120 of the first stratum 1100 may be formed of other biocompatible materials including biocompatible polymers, which may or may not be microporous, including, but not limited to, polyurethane, silicone, polysulfone, polyvinylidene fluoride (PVDF), polyhexafluoropropylene (PHFP), perfluoroalkoxy polymer (PFA), polyolefin, fluorinated ethylene propylene (FEP), acrylic copolymers and polytetrafluoroethylene (PTFE).

The first and/or second membrane layers may be in the form of one or more sheets or films, and they may include knitted, woven, and/or non-woven forms including individual or multi-fiber strands. In some embodiments, the first and/or second membrane layers 1110 and 1120 may be formed from a plurality of sheets or films of polymer material. In some embodiments, the sheets or films may be laminated or otherwise mechanically coupled together to form the first and/or second membrane layers 1110 and 1120 of the first stratum 1100. Coupling of the sheets or films may be accomplished by a variety of mechanisms, including heat treatment, high pressure compression, bonding agents such as one or more adhesives, lamination, or other suitable methods known to one of skill in the art.

In some embodiments, adjacently-situated membrane layers (e.g., first and second membrane layers 1110 and 1120) and/or the layers of material forming such membrane layers, may be partially or completely bonded via thermal methods where each of the polymers forming the materials are brought to or above their melting temperatures. In some embodiments, such thermal processes facilitate adhesive or cohesive bond formation between the materials or layers of material. In some embodiments, adjacently situated membrane layers and/or the layers of material forming such membrane layers, may be partially or completely bonded via thermal methods where at least one of the materials is brought to or above its melting temperature. Such thermal processes may facilitate adhesive or cohesive bond formation between the materials or layers of material. In some embodiments, one or more suitable adhesives are utilized and provide a sufficiently bonded interface. Adjacently situated membrane layers and/or the layers of material forming such membrane layers may be coupled together at one or more discrete locations to form stabilizing structures that extend through the resulting structure.

In some embodiments, the first stratum 1100, and/or the first and second membrane layers 1110 and 1120, and/or the sheets or films from which the first and second membrane layers 1110 and 1120 are formed may be subjected to one or more processes to modify a microstructure thereof. In some embodiments, such processes include, but are not limited to, material coating processes, surface pre-conditioning processes, and/or perforation processes. Material coating processes may be utilized to apply one or more drug or antimicrobial coatings to the polymer material (such as metallic salts (e.g. silver carbonate) and organic compounds (e.g. chlorhexidine diacetate). Hydrophilic coatings to enable wetout—including immediate wetout—of the polymer matrix can also be applied as polymer surfaces that are generally hydrophobic in nature. Surface coatings including antioxidant components can additionally or alternatively be applied to mitigate the body's inflammatory response that naturally occurs during wound healing after surgery. Material surfaces can additionally or alternatively be modified with anti-proliferative compounds (e.g., Mitomycin C, 5-fluoracil) to moderate the surrounding tissue response.

In some embodiments, one or more surface pre-conditioning processes may be utilized to form layers exhibiting an exemplary microstructure (e.g., wrinkles, folds, or other geometric out-of-plane structures), as explained in U.S. Pat. No. 9,849,629 to Zaggl. Such surface pre-conditioning could facilitate a bolder early inflammatory phase after surgery, providing an early stable interface between porous device and tissue. In some embodiments, a heparin coating may additionally or alternatively be applied to help minimize cell formation including fibrinogen buildup following a surgical implantation procedure.

In some embodiments, one or more perforation processes may be utilized to form a plurality of perforations or pores in one or more of the first and second membrane layers 1110 and 1120 of the first stratum 1100 to achieve a desired porosity. That is, one or more perforation processes may be utilized in addition to a reliance on any interstices, pores (voids between fibril and nodes making up the microstructure), and/or channels naturally occurring within the polymer material.

It will be appreciated that the first and second membrane layers 1110 and 1120 of the first stratum 1100 may be processed differently to achieve membrane layers having different material properties, such as different porosities and/or different cellular infiltration potential. In some embodiments, the first and second membrane layers 1110 and 1120 of the first stratum may not by subjected to any processing steps.

In some embodiments, the first membrane layer 1110 (also referred to herein as a medicament metering membrane layer) is configured to meter a rate at which a medicament passes through the first membrane layer 1110 and thus a rate at which a medicament is released by the medicament delivery system 1000. In various embodiments, the first membrane layer 1110 is also configured to resist cellular infiltration and attachment. In some embodiments, the first membrane layer 1110 includes interstices, perforations, pores, channels, or combinations thereof that are sized and shaped to resist, impede, or otherwise minimize cellular infiltration while remaining permeable to one or more medicaments. The interstices, perforations, pores, or channels of the first membrane layer 1110 of the first stratum 1100 may be less than (or have an average size of less than) about one (1) to about two (2) microns, for example, although a variety of dimensions may be selected based upon application. By being resistant to cellular ingrowth and attachment, the first membrane layer 1110 of the first stratum 1100 operates to maintain a separation between the medicament disposed within the medicament reservoir 1300 and the tissue surrounding the medicament delivery system 1000. This separation operates to maintain a controlled and stable rate at which medicament is released by the medicament delivery system 1000.

The second membrane layer 1120 (also referred to herein as an ingrowth membrane layer) is configured to promote or permit cellular infiltration and attachment. The second membrane layer 1120 thus generally includes interstices, perforations, pores, channels, or combinations thereof that are sized and shaped to promote or permit cellular infiltration. Thus, the second membrane layer 1120 generally includes interstices, perforations, pores, channels or combinations thereof having an average size that exceeds an average size of the interstices, perforations, pores, or channels of the first membrane layer 1110 of the first stratum 1100. In some embodiments, the second membrane layer 1120 may include interstices, perforations, pores, or channels that range in size (or average size) from between twenty (20) microns and one hundred (100) microns, although a variety of dimensions are contemplated. For example, the size (or average size) of the interstices, perforations, pores, or channels may exceed one hundred fifty (150) microns in other embodiments. Thus, while the first membrane layer 1110 operates to meter and maintain a controlled and stable rate at which medicament is released by the medicament delivery system 1000, the second membrane layer 1120 helps facilitate biointegration of the medicament delivery system 1000 by permitting cellular ingrowth and tissue attachment. Cellular ingrowth and tissue attachment helps minimize micro-movement.

In some embodiments, the interface between the first and second membrane layers 1110 and 1120 of the first stratum 1100 operates as a boundary to cellular infiltration into the first membrane layer 1110. That is, in some embodiments, the first stratum 1100 is configured such that cellular infiltration and proliferation is limited to within the second membrane layer 1120, and not into the first membrane layer 1110. Thus, in various embodiments, cellular infiltration and proliferation within the second membrane layer 1120 can generally propagate up to the boundary between the first and second membrane layers 1110 and 1120. In some embodiments, the first stratum 1100 may be configured to prevent or otherwise minimize a potential for cellular infiltration and proliferation across the boundary between the first and second membrane layers 1110 and 1120 of the first stratum 1100.

It should also be appreciated that while the first stratum 1100 (and the corresponding first and second membrane layers 1110 and 1120 of the first stratum 1100) of the medicament delivery system 1000 shown in the accompanying figures are ovularly shaped, the first and second membrane layers 1110 and 1120 and thus the first stratum 1100 may be formed of other shapes and/or sizes provided that the medicament delivery system 1000 effectively fulfills its intended purpose of being implantable within a tissue, such as a subconjunctival pocket, and operable to cause a release of a medicament disposed within the medicament reservoir 1300 of the medicament delivery system 1000 to one or more regions of the tissue surrounding the medicament delivery system 1000. For instance, the first and second membrane layers 1110 and 1120 and thus the first stratum 1100 may be square, rectangular, trapezoidal, or any other polygonal or non-polygonal shape (e.g., bean-shaped) as desired, provided the shape does not prohibit implantation or render the medicament reservoir 1300 incapable of dispensing medicament.

As shown in FIGS. 2 and 3, the second stratum 1200 of the medicament delivery system 1000 includes a first membrane layer 1210 and a second membrane layer 1220. The first membrane layer 1210 of the second stratum 1200 is similar to the first membrane layer 1110 of the first stratum 1100 in that the first membrane layer 1210 of the second stratum 1200 is configured to meter a rate at which a medicament passes through the first membrane layer 1210 and thus a rate at which a medicament is released by the medicament delivery system 1000. In various embodiments, the first membrane layer 1210 is also configured to resist cellular infiltration and attachment. The first membrane layer 1210 thus generally includes interstices, perforations, pores, channels, or combinations thereof consistent with those discussed above for the first membrane layer 1110 of the first stratum 1100.

The second membrane layer 1220 the second stratum 1200 is similar to the second membrane layer 1120 of the first stratum 1100 in that the second membrane layer 1220 of the second stratum 1200 is configured to promote or permit cellular infiltration and attachment. The second membrane layer 1220 thus generally includes interstices, perforations, pores, channels, or combinations thereof consistent with those discussed above for the second membrane layer 1120 of the first stratum 1100. Thus, in various embodiments, the medicament delivery system 1000 includes a second stratum 1200 that is formed of a first membrane layer 1210 and a second membrane layer 1220 where the first membrane layer 1210 is permeable to a medicament and configured to resist cellular infiltration and tissue attachment and where the second membrane layer 1220 is permeable to the medicament and configured to promote or permit cellular infiltration and tissue attachment.

In some embodiments, the interface between the first and second membrane layers 1210 and 1220 of the second stratum 1200 operates as a boundary to cellular infiltration into the first membrane layer 1210. That is, in some embodiments, the second stratum 1200 is configured such that cellular infiltration and proliferation is limited to the second membrane layer 1220, and not into the first membrane layer 1210. Thus, in various embodiments, cellular infiltration and proliferation within the second membrane layer 1220 can generally propagate up to, but not through, the boundary between the first and second membrane layers 1210 and 1220. In some embodiments, the second stratum 1200 may be configured to prevent or otherwise minimize a potential for cellular infiltration and proliferation across the boundary between the first and second membrane layers 1210 and 1220 of the second stratum 1200. It should be appreciated that the second stratum 1200 may include membrane layers in addition to the first and second membrane layers 1210 and 1220.

Similar to the first stratum 1100 mentioned above, the second stratum 1200 may be formed of shapes and/or sizes other than those depicted in the accompanying figures (e.g., square, rectangular, trapezoidal, bean-shaped, or any other polygonal or non-polygonal shape) provided that the medicament delivery system 1000 effectively fulfills its intended purpose of being implantable within a tissue and operable to cause a release of a medicament disposed within the medicament reservoir 1300 to one or more regions of the tissue surrounding the medicament delivery system 1000.

As shown in FIGS. 2 and 3, the first stratum 1100 is oriented such that the first membrane layer 1110 is situated adjacent the second stratum 1200 (and the first membrane layer 1210 of the second stratum 1200 in particular), and includes a first face 1102 that faces or is otherwise exposed to the second stratum 1200 (and the first membrane layer 1210 of the second stratum 1200 in particular). That is, in some embodiments, the first stratum 1100 is situated such that the first membrane layer 1110 is positioned between the second membrane layer 1120 and the second stratum 1200. Such a configuration provides that the first membrane layer 1110 of the first stratum 1100 at least partially defines the medicament reservoir 1300. That is, in various embodiments, the medicament reservoir 1300 is defined, at least in part, by one or more medicament metering membrane layers (e.g., first membrane layer 1110) that are configured to meter a rate at which a medicament is released from the medicament reservoir 1300. Such a configuration also provides that the second membrane layer 1120 of the first stratum 1100 includes a second face 1104 opposite the first face 1102 and partially defines an exterior of the medicament delivery system 1000. That is, in various embodiments, an exterior of the medicament delivery system 1000 is defined, at least in part, by one or more tissue ingrowth membrane layers (e.g., second membrane layer 1120), which are configured to promote or permit cellular infiltration and tissue attachment, as mentioned above. Promoting or permitting tissue ingrowth and attachment along one or more of the exterior surfaces of the medicament delivery system 1000 helps minimize micro-movement between the medicament delivery system 1000 and the surrounding tissue with which the medicament delivery system 1000 interfaces.

Similarly, as shown in FIGS. 2 and 3, the second stratum 1200 is oriented such that the first membrane layer 1210 of the second stratum 1200 is situated adjacent the first stratum 1100 (and the first membrane layer 1110 of the first stratum 1100 in particular), and includes a first face 1202 that faces or is otherwise exposed to the first stratum 1100 (and the first face 1102 of the first membrane layer 1210 of the first stratum 1100 in particular). That is, in some embodiments, the second stratum 1200 is situated such that the first membrane layer 1210 is positioned between the second membrane layer 1220 and the first stratum 1100. Such a configuration provides that the first membrane layer 1210 of the second stratum 1200 at least partially defines the medicament reservoir 1300. Such a configuration also provides that the second membrane layer 1220 of the second stratum 1200 includes a second face 1204 opposite the first face 1202 and partially defines an exterior of the medicament delivery system 1000. Thus, as shown in FIGS. 2 and 3, an exterior of the medicament delivery system 1000 is defined, at least in part, by the second membrane layers 1120 and 1220 of the first and second strata 1100 and 1200, respectively. Additionally, as shown in FIGS. 2 and 3, the medicament reservoir 1300 is defined, in part, by the first membrane layers 1110 and 1210 of the first and second strata 1100 and 1200, respectively. As shown, the medicament reservoir 1300 is defined by those portions of the first membrane layers 1110 and 1210 of the first and second strata 1100 and 1200 that remain uncoupled or that are not otherwise coupled to one another and that are situated radially inwardly of those portions of the first membrane layers 1110 and 1210 of the first and second strata 1100 and 1200 that are coupled together.

In various embodiments, the first and second strata 1100 and 1200 (including the various membrane layers thereof) may be connected or coupled to one another according to known methods, such as by way of heat treatment, high pressure compression, bonding agents such as one or more adhesives, combinations thereof, or other techniques known to those of skill in the art.

In some embodiments, the first faces 1102 and 1202 of the first and second strata 1100 and 1200, respectively, are coupled along the peripheral edge 1002 of the medicament delivery system 1000 such that one or more portions of the first faces 1102 and 1202 of the first and second strata 1100 and 1200 remain uncoupled to one another. In some embodiments, such uncoupled regions remain free to slide, translate, actuate, separate, or otherwise move relative to one another. This relative motion between the uncoupled or unbonded portions of the first and second strata 1100 and 1200 provides that a volume of the medicament reservoir 1300 may vary with an amount of medicament present in the medicament reservoir 1300. For example, the medicament delivery system 1000 may be transitionable between states or configurations, including a first configuration where the medicament reservoir 1300 has a first volume and a second configuration where the medicament reservoir 1300 has a second volume greater than the first volume.

FIG. 3 shows the medicament delivery system 1000 in a first configuration where the medicament reservoir 1300 is deflated (e.g., devoid of or including a negligible amount of medicament), while FIG. 2 shows the medicament delivery system 1000 in a second configuration where the medicament reservoir 1300 is inflated (e.g., full or at least partially filled with medicament). In some embodiments, the medicament delivery system 1000 adopts a relatively flat profile (e.g., a relatively uniform cross section) in a deflated state, in comparison to a profile of the medicament delivery system 1000 in an inflated state. For example, as shown in FIG. 4, the medicament delivery system 1000 may adopt a blister or pillow shape in an inflated state. However, the medicament delivery system 1000 may be configured to adopt any desirable shape or size when devoid of any medicament and/or when filled with medicament.

As the medicament delivery system 1000 is configured to deliver medicament, and because the medicament delivery system 1000 can be refilled or emptied in situ, it will be appreciated that the medicament delivery system 1000 is transitionable between the first and second configurations in situ.

Moreover, the medicament reservoir 1300 may be accessed in situ by way of a cannula, needle or other suitable instrument or method, to add or remove medicament from the medicament reservoir 1300.

The medicament delivery system 1000 shown in FIG. 2 is configured such that medicament is meterable and dispensable from the medicament delivery system 1000 through both the first and the second strata 1100 and 1200. That is, in some embodiments, the medicament delivery system 1000 includes a first and second strata 1100 and 1200 that are permeable to a medicament. In particular, in some embodiments, medicament is released from the medicament delivery system 1000 by passing through the first membrane layers 1110 and 1210 of the first and second strata 1100 and 1200, respectively, and through the second membrane layers 1120 and 1220 of the first and second strata 1100 and 1200, respectively.

Figure 5:
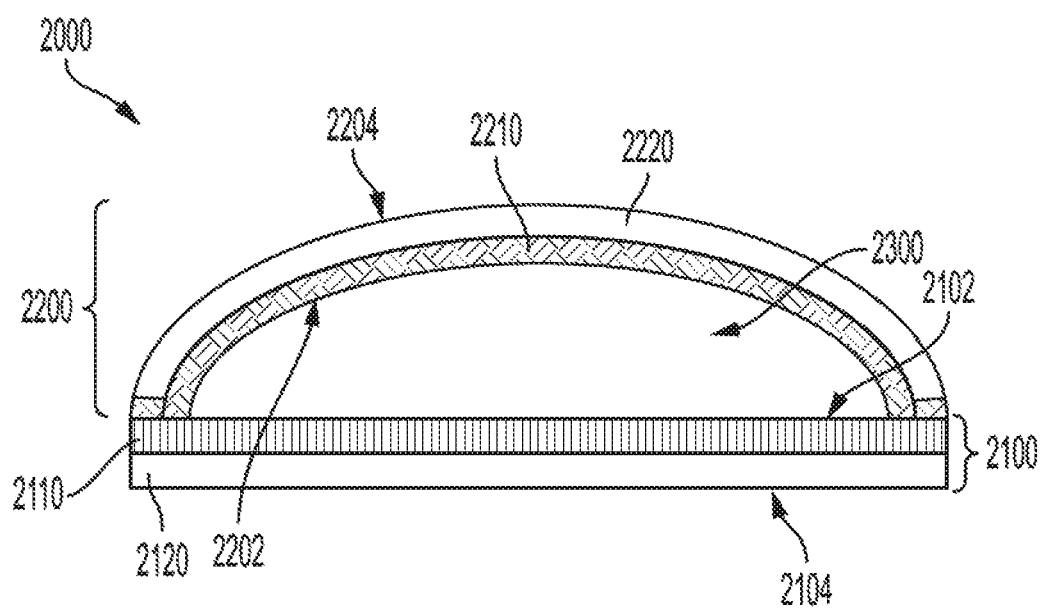
FIG. 5 is a cross-sectional view of a medicament delivery system according to some embodiments.

However, in other embodiments, the medicament delivery system may be configured such that medicament is metered and dispensed from the medicament delivery system through one or the other of the first and second strata, but not both. That is, in some embodiments, the medicament delivery system may be configured such that a first one of the first and second strata is permeable to a medicament, while the other of the first and second strata is impermeable to the medicament. For example, turning now to FIG. 5, a medicament delivery system 2000 is shown and includes a medicament permeable first stratum 2100 and a medicament impermeable second stratum 2200. The first stratum 2100 of the medicament delivery system 2000 shown in FIG. 5 is similar to the first stratum 1100 shown in FIGS. 2-4, in that it includes a first membrane layer 2110 (similar to first membrane later 1110) and a second membrane layer 2120 (similar to second membrane later 1120), where the first membrane layer 2110 is permeable to the medicament and is configured to meter a release rate of the medicament disposed within the medicament reservoir 2300 over a designated period of time and is configured to resist cellular infiltration and tissue attachment, and where the second membrane layer 2120 is permeable to the medicament and configured to promote or permit cellular infiltration and tissue attachment. Like the first stratum 1100 of the medicament delivery system 1000 referred to above, the first stratum 2100 of the medicament delivery system 2000 includes a first face 2102 and a second face 2104.

The second stratum 2200 of the medicament delivery system 2000 shown in FIG. 5 includes a first face 2202 and a second face 2204, and is formed of a first membrane layer 2210 and a second membrane layer 2220, where the first membrane layer 2210 is impermeable to medicament. The second membrane layer 2220 of the medicament delivery system 2000 shown in FIG. 5 is similar to the second membrane layer 1220 shown in FIGS. 2-4 in that the second membrane layer 2220 shown in FIG. 5 is configured to promote or permit cellular infiltration and tissue attachment. However, unlike previous examples, the first membrane layer 2210 is impermeable to the medicament disposed within the medicament reservoir 2300. Alternatively, the medicament delivery system 2000 may be configured such that the first stratum 2100 is medicament impermeable while the second stratum 2200 is medicament permeable. The medicament permeable stratum (e.g., first or second strata 2100 or 2200) may include a first medicament permeable membrane layer that is configured to resist cellular infiltration and tissue attachment and/or a second medicament permeable membrane layer that is configured to promote or permit cellular infiltration and tissue attachment. In turn, the medicament impermeable stratum (e.g., first or second strata 2100 or 2200) may include a first medicament impermeable membrane layer that is configured to resist cellular infiltration and tissue attachment and/or a second medicament impermeable membrane layer that is configured to promote or permit cellular infiltration and tissue attachment.

With continued reference to FIG. 5, the second membrane layer 2220 may be formed of any biocompatible material discussed herein, such as a biocompatible polymer, which is further combined with an elastomer or elastomeric material to form a composite material that is impermeable to the medicament. For instance, the second membrane layer 2220 may include a composite material that includes a microporous polymeric membrane having nodes and fibrils where pores are the spaces within the matrix of fibrils (e.g., ePTFE) and a sealing material, such as an elastomeric material, present therein. In some embodiments, the sealing material may be imbibed into the polymeric membrane to form a medicament impermeable membrane layer. It should be appreciated that multiple types of fluoropolymer (and non-fluoropolymer) membranes and multiple types of elastomeric materials can be combined to form a composite material while remaining within the scope of the present disclosure. It should also be appreciated that the elastomeric material can include multiple elastomers as well as multiple types of non-elastomeric components, such as inorganic fillers, therapeutic agents, radiopaque markers, and the like while remaining within the scope of the present disclosure.

In some embodiments, the various membrane layers are formed of expanded polytetrafluoroethylene (ePTFE), although other biocompatible polymers suitable for use in forming medicament impermeable membrane layers including, but not limited to, urethanes, silicones (organopolysiloxanes), copolymers of silicon-urethane, styrene/isobutylene copolymers, polyisobutylene, polyethylene-co-poly (vinyl acetate), polyester copolymers, nylon copolymers, fluorinated hydrocarbon polymers and copolymers or mixtures of any of the foregoing may be used.

In various embodiments, the elastomer or elastomeric material may include perfluoromethyl vinyl ether and tetrafluoroethylene, (per)fluoroalkylvinylethers (PAVE), a copolymer of tetrafluoroethylene and perfluoromethyl vinyl ether, silicone, a fluoroelastomer, a urethane, or a TFE/PMVE copolymer.

With continued reference to the medicament delivery system 2000 shown in FIG. 5, by including a medicament permeable first stratum 2100 and a medicament impermeable second stratum 2200, the medicament delivery system 2000 can be configured to unidirectionally meter and dispense the medicament disposed within the medicament reservoir 2300. That is, in some embodiments, the medicament delivery system 2000 can be configured such that medicament is metered and released through one of the first and second strata 2100 and 2200, but not through the other of the first and second strata 2100 and 2200. Thus, in these embodiments, the medicament delivery system 2000 can be configured such that the medicament is released in a first direction (e.g., through the first stratum 2100) without also releasing the medicament in a second direction (e.g., through the second stratum 2200). Providing this type of controlled release helps provide for directing the dispensing of medicament to a designated tissue. For example, medicament can be released in a direction toward scleral tissue, while minimizing the release of medicament in a direction toward conjunctival tissue, which may be useful is treating conditions within an interior of the eye. Alternatively, medicament can be released in a direction toward conjunctival tissue, while minimizing the release of medicament in a direction toward scleral tissue, which may be useful in treating other conditions of the eye, such as conditions affecting the exterior of the eye (e.g., dry eye). Releasing medicament in a direction toward conjunctival tissue may be used for treating other areas or regions of the body as medicament dispensed to the conjunctiva may be absorbed by the surrounding vasculature and transported to other regions of a patient's anatomy. It should be appreciated that the terms first and second, as used herein with regard to the first and second strata 2100 and 2200, are generic identifiers and thus the strata 2100 and 2200 may be referred to in conjunction with alternative generic identifiers such as top, bottom, upper, lower, side, and so forth. Accordingly, although the stratum 2100 is referred to above in conjunction with the term "first," and the stratum 2200 is referred to above in conjunction with the term "second," it should be appreciated that the strata 2100 and 2200 may alternatively be referred to as the first stratum 2200 and the second stratum 2100. That is, the terms "first" and "second" should not be understood to represent anything more than generic identifiers for strata 2100 and 2200.

Figure 6:
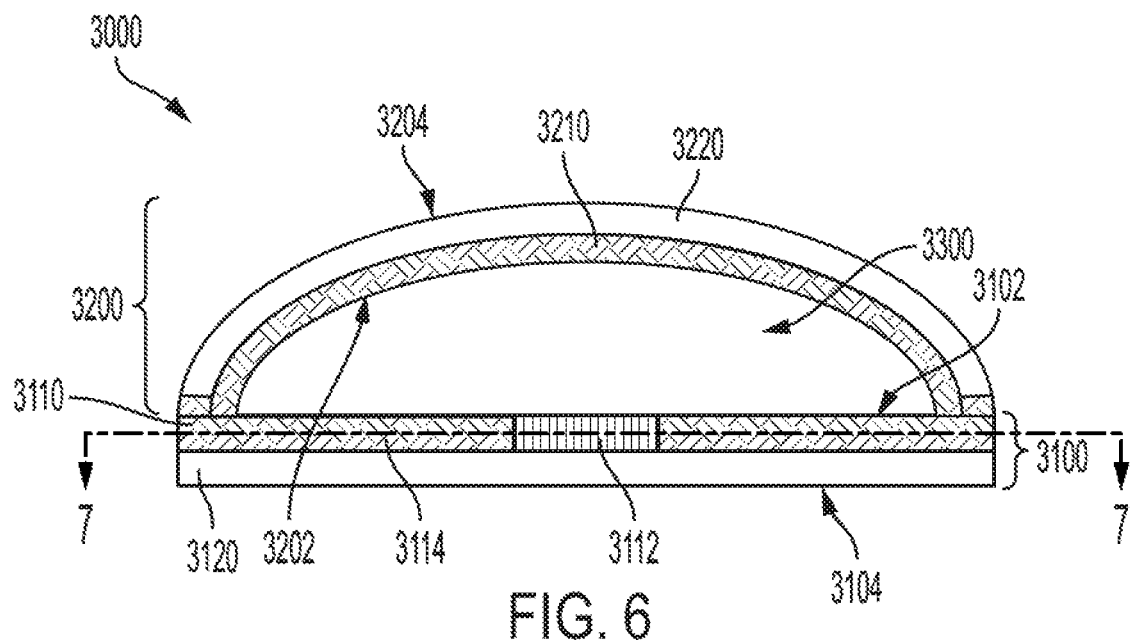
FIG. 6 is a cross-sectional view of a medicament delivery system according to some embodiments.
Figure 7:
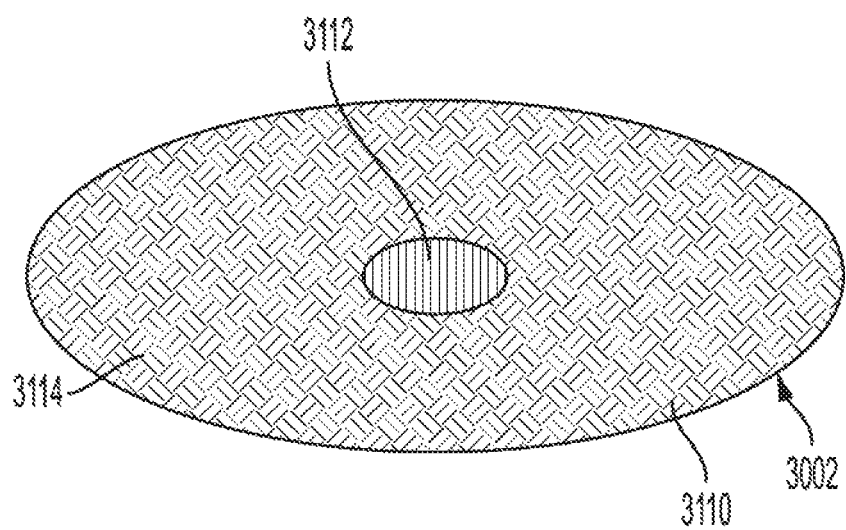
FIG. 7 is a cross-sectional view of the medicament delivery system illustrated in FIG. 6 taken along line 7-7 according to some embodiments.

In some embodiments, one or more of the first and second strata may be configured to include one or more medicament permeable portions and one or more medicament impermeable portions. Turning now to FIGS. 6 and 7, a medicament delivery system 3000 is shown, and includes a first stratum 3100 and a second stratum 3200. The second stratum 3200 is consistent in form and construction with the second stratum 2200 of the medicament delivery system 2000 illustrated in FIG. 5 and described above, and includes a first membrane layer 3210, a second membrane layer 3220, a first face 3202, and a second face 3204. The first stratum 3100, on the other hand, is different from previous first stratum examples in that the first stratum 3100 shown in FIGS. 6 and 7 includes a first membrane layer 3110 having a first portion 3112 that is permeable to the medicament and a second portion 3114 that is impermeable to medicament. The first membrane layer 3110 is configured to meter a release rate of the medicament disposed within the medicament reservoir 1300 over a designated period of time. The second membrane layer 3120 is similar to the second membrane layer 3120 of the medicament delivery system 1000 shown in FIG. 5 discussed above.

In various embodiments, the first portion 3112 of the first membrane layer 3110 generally includes interstices, perforations, pores, channels, or other release features that are sized and shaped to allow medicament disposed within the medicament reservoir 3300 to be released through the first portion 3112. In some embodiments, metering the release of the medicament disposed within the medicament reservoir 3300 by the first stratum 3100 may be tuned or otherwise controlled by increasing (or alternatively decreasing) a surface area of the metering first portion 3112 of the first membrane layer 3110. In some embodiments, increasing a surface area of the metering first portion 3112 from a first surface area to a second larger surface area is associated with an increase of an amount of medicament released by the medicament delivery system 3000 per unit of time. Similarly, decreasing a surface area of the metering first portion 3112 from a first surface area to a second smaller surface area is associated with a decrease of an amount of medicament released by the medicament delivery system 3000 per unit of time.

For example, if a medicament delivery system includes a medicament reservoir having a first size (e.g., volume) and a first medicament metering membrane layer having a first surface area and including a first material having a first release rate per unit area, then the medicament delivery system is associated with a first medicament release rate per unit time and with metering a release of the medicament for a first period of time. If the size of the medicament reservoir is increased from the first size to a second, larger size while maintaining the first surface area and the first material of the metering membrane layer, then it should be appreciated that the medicament delivery system is operable to meter a release of medicament for a second period of time longer than the first period of time. On the other hand, if the first surface area of the metering membrane layer is decreased to a second, decreased surface area while the first material of the metering membrane layer and the first size of the medicament reservoir are maintained, then it should be appreciated that the medicament delivery system is operable to meter a release of medicament for a third period of time longer than the first period of time. Additionally, if the first material of the metering membrane layer is changed to a second material which has a second, decreased release rate per unit area, while the first size of the medicament reservoir and the first surface area of the metering membrane layer are maintained, then it should be appreciated that the medicament delivery system is operable to meter a release of medicament for a fourth period of time longer than the first period of time. Combinations of the above concepts may be utilized to maintain a medicament release period while increasing an amount of medicament released per unit of time. For example, if the size of the medicament reservoir is increased from the first size to a second, larger size in combination with an increase in the surface area of the metering membrane layer from the first surface area to a second, increased surface area while maintaining the first material of the metering membrane layer, then it should be appreciated that the medicament delivery system is operable to increase an amount of medicament released during the first period of time.

It is to also be appreciated that different materials may possess different flow rates per unit area, based for example of differing microstructures (e.g., increased quantity and/or size of interstices, perforations, pores, channels or other release features present in the microstructure). Thus, different materials may be additionally or alternatively selected to tune or otherwise control the degree or amount by which the release of the medicament disposed within the medicament reservoir is metered.

The various medicament delivery systems discussed herein thus provide for configurations including a relatively large medicament reservoir without also inherently possessing a high release rate of medicament due to an associated large medicament metering surface area, or alternatively, a relatively small medicament reservoir without also inherently possessing a low release rate of medicament due to an associated low medicament metering surface area. A relatively large medicament reservoir in combination with a low release rate provides for a medicament delivery system 1000 that can be implanted for long periods of time (e.g., weeks, months, a year, or more) without requiring interventions to refill medicament. Conversely, a relatively small medicament reservoir in combination with a high release rate provides for a medicament delivery system that can be implanted and dispense medicament at a fast rate without being oversized and interfering with normal eye operation (e.g., blinking and eye movements).

In addition, it should be appreciated that medicaments having coarser molecular structures generally require that the medicament delivery system include a microstructure having interstices, pores, channels and/or other release features that correspond in size such that the medicament can pass through the material of the medicament metering membrane layer. Thus, it will be appreciated that different medicament delivery systems may be selected for use in administering different medicaments.

With continued reference to the medicament delivery system 3000 shown in FIGS. 6 and 7, the first membrane layer 3110 of the first stratum 3100 may be formed of one or more sheets or films of material, such as any biocompatible material discussed herein), but where the one or more sheets or films of material have been further combined with a sealing material, such as an elastomer or elastomeric material, in the medicament impermeable second portions 3114. Thus, in some embodiments, the medicament impermeable second portions 3114 of the first membrane layer 3110 of the first stratum 3100 may include a composite structure. In some embodiments, the medicament impermeable second portions 3114 of the first membrane layer 3110 of the first stratum 3100 may correspond with portions of the first membrane layer 3110 of the first stratum 3100 that have been selectively imbibed with and/or coated with a sealing material. That is, in various embodiments, first membrane layer 3110 of the first stratum 3100 may be configured such that one or more portions of the first membrane layer 3110 include a sealing material and where one or more other portions of the first membrane layer 3110 remain free of a sealing material, where those portions of the first membrane layer 3110 that include the sealing material correspond with the medicament impermeable second portions 3114, and where those portions of the first membrane layer 3110 that do not include the sealing material correspond with the medicament metering first portions 3112.

While the medicament delivery system 3000 shown in FIGS. 6 and 7 includes an ovularly shaped medicament metering first portion 3112, the medicament metering first portion 3112 may be formed of other shapes and/or sizes other than those depicted in the accompanying figures (e.g., square, rectangular, trapezoidal, bean-shaped, or any other polygonal or non-polygonal shape) provided that the medicament metering first portion 3112 effectively fulfills its intended purpose of metering a release of the medicament. Thus, it is to be appreciated that a boundary defined between the medicament metering first portion 3112 and the medicament impermeable second portion 3114 may be define any suitable shape consistent with the above.

It should also be appreciated that while the medicament delivery system 3000 shown in FIG. 7 includes only a single, centrally located medicament metering first portion 3112, the first membrane layer 3110 of the first stratum 3100 may include a plurality of discrete medicament metering first portions 3112. Similarly, it should be appreciated that the medicament metering first portion 3112 of the first membrane layer 3110 of the first stratum 3100 need not be centrally located, but may instead be positioned at a location offset from a central position.

In various embodiments, a medicament delivery system may be configured such that one or more of the medicament metering membrane layers discussed herein may be exposed to a tissue surface of the patient's anatomy. For example, turning now to FIGS. 8 and 9, a medicament delivery system 4000 is shown, and includes a first stratum 4100 and a second stratum 4200. The second stratum 4200 is similar to the second stratum 2200 of the medicament delivery system 2000 shown in FIG. 5 and discussed above, in that the second stratum 4200 is impermeable to the medicament and includes a medicament impermeable first membrane layer 4210 and a second membrane layer 4220 that is configured to promote or permit cellular infiltration and tissue attachment. Similar to the medicament delivery system 2000 shown in FIG. 5 the second stratum 4200 includes a first face 4202 and a second face 4204.

Figure 8:
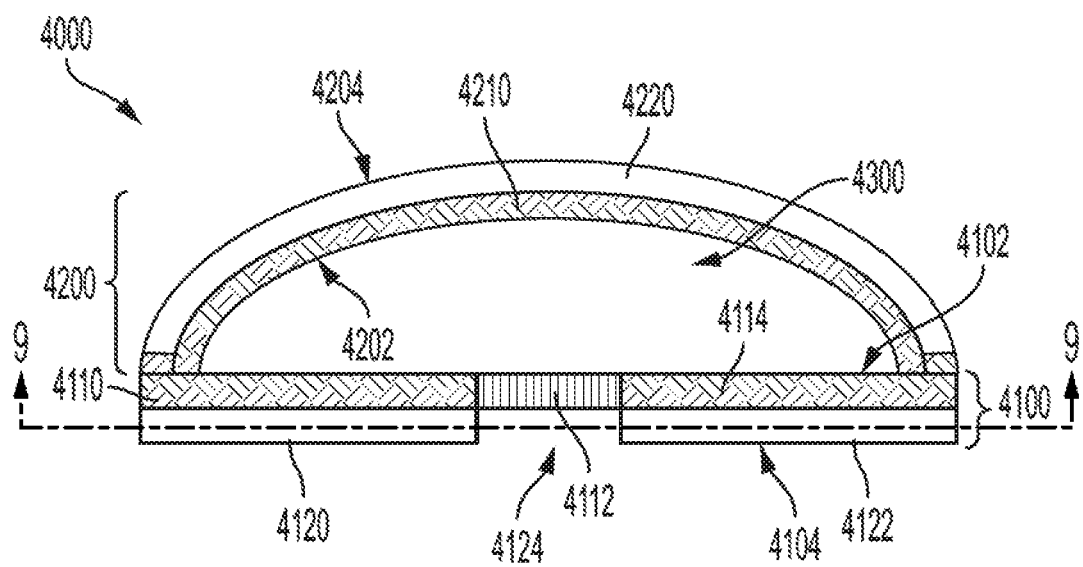
FIG. 8 is a cross-sectional view of a medicament delivery system according to some embodiments.
Figure 9:
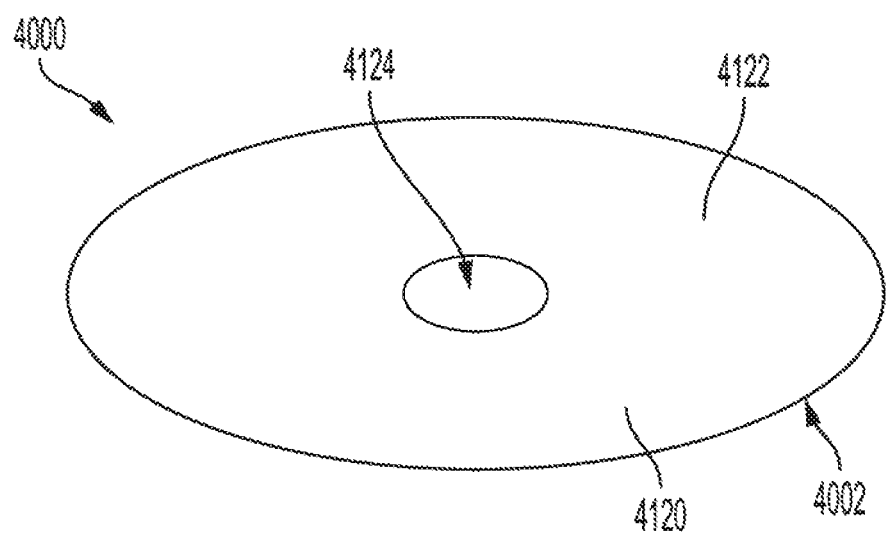
FIG. 9 is a cross-sectional view of the medicament delivery system illustrated in FIG. 8 taken along line 9-9 according to some embodiments.

The first stratum 4100 shown in FIGS. 8 and 9 differs, however, from the previous first stratum examples in that the first stratum 4100 shown in FIGS. 8 and 9 includes an aperture or relief which exposes a portion of the first membrane layer 4110. First membrane layer 4110 is configured to meter a release rate of the medicament disposed within the medicament reservoir 4300 over a designated period of time. In particular, as shown in FIGS. 8 and 9, the second membrane layer 4120 includes an aperture 4124 formed in a body 4122 of the second membrane layer 4120, where the aperture 4124 in the second membrane layer 4120 of the first stratum 4100 operates to expose the first membrane layer 4110. When implanted, one or more portions of the first membrane layer 4110 of the first stratum 4100 are directly exposed to tissue, while the second membrane layer 4120 operates to maintain a separation between the first membrane layer 4110 and the tissue surface.

Direct exposure of the first membrane layer 4110 of the first stratum 4100 helps enable more effective and efficient drug delivery to tissue. Maintaining a separation between the first membrane layer 4110 and a tissue surface helps minimize micro-movement between the first membrane layer 4110 and the tissue. As discussed above, minimizing micro-movement helps minimize micro-irritations.

Thus, in various embodiments, the medicament delivery system 4000 includes a medicament permeable first stratum 4100 and a medicament impermeable second stratum 4200, where the first stratum 4100 includes a first membrane layer 4110 and a second membrane layer 4120 and where the first membrane layer 4110 is permeable to a medicament and configured to resist cellular infiltration and tissue attachment and where the second membrane layer 4120 is permeable to the medicament and configured to promote or permit cellular infiltration and tissue attachment and where the second membrane layer 4120 is configured such that one or more portions of the first membrane layer 4110 are exposed to tissue when implanted while the second membrane layer 4120 is positioned between the tissue and one or more other portions of the first membrane layer 4110 while implanted.

In some embodiments, the various medicament delivery systems discussed herein are shaped as thin, puck-shaped members. The medicament delivery systems may include thicknesses between exterior opposing surfaces of the (e.g., a distance measured between the second face 1104 of the first stratum 1100 and the second face 1204 of the second stratum 1200) of less than or equal to half of a millimeter (0.5 mm), such as between one-tenth of a millimeter (0.1 mm) and half of a millimeter (0.5 mm), for example although a variety of dimensions are contemplated. For example, given differing anatomies of the human body, the medicament delivery systems may exceed half of a millimeter (0.5 mm) without departing from the spirit or scope of the present disclosure provided that the thickness does not substantially interfere with normal eye functioning (e.g., pivoting and blinking).

In some embodiments, the various medicament delivery systems disclosed herein may have diameters (or widths across a major axis) in the range of five (5) millimeters to fifteen (15) millimeters. In a particular embodiment, the medicament delivery system disclosed herein may have a diameter (or width across a major axis) of ten (10) millimeters. In those embodiments where the medicament delivery systems are ovularly shaped, the medicament delivery systems may include a major dimension (e.g., of the oval) of up to about thirty (30) millimeters and corresponding minor dimension of up to about ten (10) millimeters. Though, as discussed above, given differing anatomies of the human body, the medicament delivery systems may exceed such dimensions (e.g., fifteen (15), and ten (10) and thirty (30) millimeters) without departing from the spirit or scope of the present disclosure provided that the size does not substantially interfere with normal eye functioning (e.g., pivoting and blinking). Likewise, the medicament delivery systems disclosed herein may include diameters (or widths across a major axis) of less than five (5) millimeters without departing from the spirit or scope of the present disclosure provided that the medicament delivery systems are operable to elute a sufficient degree of medicament for absorption by the surrounding tissue. The shapes and sizes discussed herein should not be viewed as limiting.

Additionally, while medicament delivery systems discussed above are described as including a single medicament reservoir, it is to be appreciated that any of the above-discussed medicament delivery systems may include multiple reservoirs. These reservoirs may be fluidly coupled or isolated from one another. In some embodiments, each reservoir may be configured to house a same or different medicament. Accordingly, in some embodiments, the medicament delivery systems discussed herein may be configured to deliver multiple different medicaments, either from the same reservoir, or from a plurality of different reservoirs.

Additionally, in various embodiments, it is to be appreciated that the medicament may be loaded onto or otherwise incorporated into bioabsorbable particles which help aid in metering the medicament. In some embodiments, the particles may be of a size where they can be made into a dispersion and injected or otherwise delivered to within a medicament reservoir in situ (e.g., while the medicament delivery system is implanted within the patient's eye). That is, in some examples, the medicament may be included in a fluid suspension of particles. In various embodiments, a filled or partially filled medicament microporous reservoir may be accessed in situ (e.g., via syringe or other suitable means) and the contents of the reservoir (e.g., particles) removed and/or reloaded with fresh particles to maintain a constant delivery of medication over time. In various embodiments, placement of the fluid suspension of particles within the medicament reservoir may be accomplished via a syringe or other suitable means of delivery.

In some embodiments, the medicament delivery systems discussed herein are configured such that the medicament microporous reservoir retains the particles in the medicament reservoir and permits the dispersion carrier fluid (e.g., water) to exit the reservoir through one or more strata of the medicament delivery system. For instance, in some embodiments, the material defining the medicament reservoir (e.g., one or more of the first, second, third, or fourth microporous layers) may include a microstructure that is configured to prevent the particles of the fluid suspension from passing through the material. For example, the first microporous layer may be configured to resist tissue ingrowth, and may include interstices, perforations, pores, channels, or combinations thereof that prevent the particles of the fluid suspension from passing through the material. In some embodiments, the particles are configured to break down or degrade over time such that the medicament (alone or in a solution with the fluid) can percolate, diffuse, or otherwise pass through one or more of the strata of the microporous reservoir from an interior of the medicament reservoir to an exterior of the medicament delivery system for absorption by the body. In some embodiments, a concentration of the solution of dispersion carrier fluid and particles may change or be changed over time. For example, particles may be added to the dispersion carrier fluid (e.g., in situ) to increase a concentration of particles within the reservoir. Additionally or alternatively, dispersion carrier fluid may be added to reduce a concentration of particles within the reservoir.

In some embodiments, the various medicament delivery systems disclosed herein may additionally or alternatively include one or more structural spacers, such as one or more stents, struts, and/or reinforcing element. The one or more structural spacers may be incorporated into, integrated into, coupled to, or otherwise disposed within the reservoir to maintain a separation between those microporous layers forming the reservoir. Such structural spacers may be formed of any suitable biocompatible material (e.g., natural materials, or synthetic materials such as metals and polymers) discussed herein.

The inventive scope of this application has been described above both generically and with regard to specific embodiments and examples. It will be apparent to those skilled in the art that various modifications and variations can be made in the embodiments and examples without departing from the scope of the disclosure. Likewise, the various components discussed in the embodiments and examples discussed herein are combinable. Thus, it is intended that the embodiments and examples cover the modifications and variations of the inventive scope.

What is claimed is:

1. An implantable delivery device for dispensing a medicament, the delivery device comprising: a first microporous layer including a plurality of pores sized to permit tissue ingrowth; a second microporous layer including a plurality of pores sized to permit tissue ingrowth; a third microporous layer coupled to the first microporous layer including a plurality of pores sized to resist tissue ingrowth; and a reservoir for receiving the medicament, the reservoir being defined between the third microporous layer and the second microporous layer, the reservoir having an inflated state when the reservoir is filled with a sufficient amount of the medicament and having a deflated state when the reservoir is devoid of the sufficient amount of the medicament, wherein when implanted in a body, uncoupled portions of the second and third microporous layers move toward each other when transitioning between the inflated and deflated states, such that the reservoir adopts a relatively flatter profile in the deflated state than in the inflated state, wherein at least a portion of the uncoupled portions of the second and third microporous layers are in contact when in the deflated state, wherein the third microporous layer is configured to meter a rate at which the medicament is eluted from the reservoir when the delivery device is implanted.

2. The device of claim 1, further comprising a fourth microporous layer coupled to the second microporous layer such that the reservoir is defined between the third microporous layer and the fourth microporous layer.

3. The device of claim 2, wherein the fourth microporous layer includes a plurality of pores sized to resist tissue ingrowth, and wherein the fourth microporous layer is permeable to the medicament.

4. The device of claim 2, wherein the fourth microporous layer is impermeable to the medicament.

5. The device of claim 4, wherein the fourth microporous layer includes an elastomer.

6. The device of claim 1, wherein the first microporous layer includes an aperture configured to expose the third microporous layer.

7. The device of claim 1, wherein the reservoir is configured to be refilled and emptied in situ.

8. The device of claim 1, wherein the reservoir is configured to inflate to accommodate the medicament therein.

9. The device of claim 1, wherein at least one of the first and second microporous layers comprise an expanded polytetrafluoroethylene (ePTFE) membrane.

10. The device of claim 1, wherein a first portion of the third microporous layer is impermeable to the medicament, and wherein a second portion of the third microporous layer is permeable to the medicament.

11. The device of claim 10, wherein the first portion of the third microporous layer includes an elastomer.

12. The device of claim 1, wherein the delivery device is implantable within an eye.

13. The device of claim 12, wherein the medicament is an ocular medicament for treating glaucoma.

14. The device of claim 1, wherein the medicament is included within a fluid suspension of particles.

15. The device of claim 1, wherein portions of the second microporous layer and the third microporous layer are inelastic.

16. An implantable delivery device for dispensing a medicament, the delivery device comprising: a first microporous layer coupled to a second microporous layer to define a reservoir having an inflated state and a deflated state, the first microporous layer comprising a first interior surface and an opposing second interior surface, and a body having an exterior surface, wherein the first interior surface is separable from the second interior surface when the reservoir is filled with a sufficient amount of medicament in the inflated state, wherein the first interior surface is configured to meter a dispensing of the medicament over a predetermined period of time, wherein when implanted in a body, uncoupled portions of the first and second microporous layers move toward each other when transitioning between the inflated and deflated states, such that the delivery device adopts a relatively flatter profile in the deflated state than the inflated state, wherein at least a portion of the uncoupled portions of the first and second microporous layers are in contact when in the deflated state, wherein the first interior surface is configured to resist tissue ingrowth, and wherein the exterior surface of the body is configured to permit tissue ingrowth.

17. The device of claim 16, wherein at least a portion of the first interior surface is permeable to the medicament.

18. The device of claim 16, wherein the second interior surface is impermeable to the medicament.

19. A delivery device for dispensing a medicament comprising: a microporous body including a first microporous layer, a second microporous layer, and a third microporous layer, the first microporous layer being situated between the second and third microporous layers, the first microporous layer including a plurality of pores sized to resist tissue ingrowth, where the second and third microporous layers each include a plurality of pores sized to permit tissue ingrowth; and a medicament reservoir located between the first microporous layer and the third microporous layer, the medicament reservoir having an expanded state and a collapsed state, wherein when implanted in a body, uncoupled portions of the first and third microporous layers move toward each other when transitioning between the expanded and collapsed states, such that the medicament reservoir adopts a relatively flatter profile in the collapsed state than in the expanded state, wherein at least a portion of the uncoupled portions of the first and third microporous layers are in contact when in the collapsed state.

20. The device of claim 19, wherein the first microporous layer includes a metering portion for dispensing a medicament over a period of time.

21. The device of claim 19, wherein the second and third microporous layers define an exterior of the delivery device.

22. The device of claim 19, wherein the first microporous layer is coupled to the second microporous layer.

23. The device of claim 22, wherein the second microporous layer includes an aperture configured to expose the first microporous layer.

24. A medicament metering device having an exterior surrounding an interior that defines a medicament reservoir, the device comprising: a first stratum including a first microporous layer and a second microporous layer, the first microporous layer being configured to resist tissue ingrowth and the second microporous layer being configured to permit tissue ingrowth, the first microporous layer defining a portion of the interior and the second microporous layer defining a portion of the exterior; and a second stratum coupled to the first stratum such that the medicament reservoir is defined between the first and second strata, a portion of the first microporous layer of the first stratum being permeable to a medicament disposable within the medicament reservoir, wherein the medicament reservoir has expanded state and a collapsed state, and wherein when implanted in a body, uncoupled portions of the first and second strata move toward each other when transitioning between the expanded and collapsed states, such that the medicament reservoir adopts a relatively flatter profile in the collapsed state than in the expanded state, wherein at least a portion of the uncoupled portions of the first and second strata are in contact when in the collapsed state.

25. The device of claim 24, wherein the medicament reservoir is defined between portions of the first and second strata that are not coupled to one another such that the uncoupled portions of the first and second strata are free to deflect relative to one another.

26. The device of claim 24, wherein the second stratum includes a third microporous layer and a fourth microporous layer, the third microporous layer of the second stratum being configured to resist tissue ingrowth and the fourth microporous layer of the second stratum being configured to permit tissue ingrowth, wherein the third microporous layer of the second stratum defines a portion of the interior and the fourth microporous layer defines a portion of the exterior.

* * * * *